(12) United States Patent
Gallippi et al.

(10) Patent No.: US 11,445,914 B2
(45) Date of Patent: Sep. 20, 2022

(54) METHODS AND SYSTEMS FOR ASSESSING MATERIAL ANISOTROPY AND OTHER CHARACTERISTICS

(71) Applicant: The University of North Carolina at Chapel Hill, Chapel Hill, NC (US)

(72) Inventors: Caterina M. Gallippi, Cary, NC (US); Christopher Joseph Moore, Durham, NC (US); Md Murad Hossain, Chapel Hill, NC (US); Tomasz Joseph Czernuszewicz, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 734 days.

(21) Appl. No.: 16/301,085

(22) PCT Filed: May 15, 2017

(86) PCT No.: PCT/US2017/032745
§ 371 (c)(1),
(2) Date: Nov. 13, 2018

(87) PCT Pub. No.: WO2017/197404
PCT Pub. Date: Nov. 16, 2017

(65) Prior Publication Data
US 2019/0183344 A1    Jun. 20, 2019

Related U.S. Application Data

(60) Provisional application No. 62/336,437, filed on May 13, 2016.

(51) Int. Cl.
*A61B 5/00* (2006.01)
*A61B 5/055* (2006.01)
(Continued)

(52) U.S. Cl.
CPC .............. *A61B 5/0066* (2013.01); *A61B 5/00* (2013.01); *A61B 5/0035* (2013.01);
(Continued)

(58) Field of Classification Search
CPC ......... A61B 8/48; A61B 5/0077; A61B 8/485; A61B 5/055; A61B 5/0035; A61B 5/0053;
(Continued)

(56) References Cited

U.S. PATENT DOCUMENTS 6,418,776 B1 * 7/2002 Gitis ........................ G01N 3/56
73/10
7,497,134 B2 * 3/2009 Renken .................... G01L 1/148
73/862.68
(Continued)

FOREIGN PATENT DOCUMENTS

SU          1392447     *   4/1984   ............... G01N 3/58

OTHER PUBLICATIONS

Commonly-assigned, Co-pending U.S. Appl. No. 17/176,772 for "Methods, Systems, and Computer Readable Media for Evaluating Mechanical Anisotropy for Breast Cancer Screening and Monitoring Response to Therapy," (Unpublished, filed Feb. 16, 2021).
(Continued)

*Primary Examiner* — Jacques M Saint Surin
(74) *Attorney, Agent, or Firm* — Jenkins, Wilson, Taylor & Hunt, P.A.

(57) ABSTRACT

Methods, systems, and computer readable media for taking measurements of a material, including determining material anisotropy, are provided. According to one aspect, a method for determining tissue anisotropy comprises: applying, to a tissue sample, a first force having a direction and having a coronal plane normal to the direction of the force, the first force having an oval or other profile with long and short axes
(Continued)

within the coronal plane, the long axis being oriented in a first direction within the coronal plane, and measuring a first displacement of the tissue; applying, to the tissue sample, a second force, and measuring a second displacement of the tissue; and calculating a tissue elasticity anisotropy based on the measured first and second displacements. Furthermore, by applying the first and second forces multiple times, tissue viscosity, elasticity, or other anisotropy may be calculated from the multiple displacement measurements.

19 Claims, 22 Drawing Sheets

(51) Int. Cl.

| | | |
|---|---|---|
| *G01N 29/07* | (2006.01) | |
| *G01N 29/22* | (2006.01) | |
| *G01S 15/89* | (2006.01) | |
| *G01S 7/52* | (2006.01) | |
| *A61B 8/08* | (2006.01) | |
| *G01N 29/11* | (2006.01) | |
| *A61B 5/107* | (2006.01) | |
| *G01B 15/06* | (2006.01) | |
| *G01N 11/00* | (2006.01) | |
| *G01N 29/04* | (2006.01) | |

(52) U.S. Cl.
CPC .......... *A61B 5/0053* (2013.01); *A61B 5/0057* (2013.01); *A61B 5/0077* (2013.01); *A61B 5/055* (2013.01); *A61B 5/1075* (2013.01); *A61B 8/08* (2013.01); *A61B 8/48* (2013.01); *A61B 8/485* (2013.01); *G01B 15/06* (2013.01); *G01N 11/00* (2013.01); *G01N 29/043* (2013.01); *G01N 29/07* (2013.01); *G01N 29/11* (2013.01); *G01N 29/221* (2013.01); *G01S 7/52022* (2013.01); *G01S 7/52042* (2013.01); *G01S 15/8915* (2013.01); *G01S 15/8993* (2013.01); *G01N 2291/015* (2013.01); *G01N 2291/0289* (2013.01); *G01N 2291/02475* (2013.01)

(58) Field of Classification Search
CPC ........... A61B 5/1075; A61B 8/08; A61B 5/00; A61B 5/0066; A61B 5/0057; G01N 29/07; G01N 29/221; G01N 29/11; G01N 11/00; G01N 29/043; G01N 2291/0289; G01N 2291/015; G01N 2291/02475; G01S 7/52022; G01S 15/8915; G01S 7/52042; G01S 15/8993
USPC .......................................................... 73/584
See application file for complete search history.

(56) References Cited

U.S. PATENT DOCUMENTS

| | | | | |
|---|---|---|---|---|
| 7,535,217 | B2* | 5/2009 | Quandt ...................... | G01L 9/16 324/207.2 |
| 8,753,277 | B2* | 6/2014 | McAleavey .......... | A61B 8/4483 600/437 |
| 9,211,111 | B2 | 12/2015 | Tamura | |
| 9,244,041 | B2* | 1/2016 | Gallippi ............... | G01N 29/045 |
| 10,772,608 | B2* | 9/2020 | Kanayama .............. | A61B 8/485 |
| 2003/0182069 | A1* | 9/2003 | Banes .................... | G01N 3/068 702/33 |
| 2007/0088210 | A1 | 4/2007 | Woo et al. | |
| 2011/0287948 | A1* | 11/2011 | Suresh .............. | B01L 3/502746 506/7 |
| 2013/0046175 | A1 | 2/2013 | Sumi | |
| 2013/0181722 | A1 | 7/2013 | Pfaff | |
| 2014/0046187 | A1 | 2/2014 | Taniguchi et al. | |
| 2015/0320394 | A1 | 11/2015 | Arnal et al. | |
| 2015/0362564 | A1 | 12/2015 | Wan et al. | |
| 2021/0239775 | A1* | 8/2021 | Gallippi ................. | G01R 33/58 |
| 2021/0259657 | A1* | 8/2021 | Gallippi ............... | A61B 8/0825 |
| 2021/0293677 | A1 | 9/2021 | Gallippi et al. | |

OTHER PUBLICATIONS

Commonly-assigned, Co-pending U.S. Appl. No. 17/150,612 for "Methods, Systems, and Computer-Readable Media for Nondestructively Quantitatively Measuring Physical Properties of a Material by Observing Induced Displacements Using Different Focal Configurations," (Unpublished, filed Jan. 15, 2021).

Hossain et al., "Viscoelectric Response Ultrasound Derived Relative Elasticity and Relative Viscosity Reflect True Elasticity and Viscosity: In Silico and Experimental Demonstration," IEEE Transactions on Ultrasonics, Ferroelectrics, and Frequency Control, vol. 67, No. 6, pp. 1102-1117 (Jun. 2020).

Zhang et al., "Fluidity and elasticity form a concise set of viscoelastic biomarkers for breast cancer diagnosis based on Kelvin-Voigt fractional derivative modeling," Springer, pp. 1-16 (Apr. 25, 2020).

Torres et al., "Viscoelastic Response (VisR)-Derived Mechanical Anisotropy for Differentiating Malignant from Benign Breast Lesions in Women, in vivo," 2019 IEEE International Ultrasonic Symposium (IUS), pp. 1-3 (2019).

You et al., "Quantitative and Qualitative Evaluation of Breast Cancer Prognosis: A Sonographic Elastography Study," Med Sci Monit, vol. 25, pp. 1-8 (2019).

Sood et al., "Ultrasound for Breast Cancer Detection Globally: A Systematic Review and Meta-Analysis," Journal of Global Oncology, pp. 1-17 (Aug. 27, 2019).

Nabavizadeh et al., "Viscoelastic biomarker for differentiation of benign and malignant breast lesion in ultra-low frequency range," Scientific Reports, vol. 9, No. 5737, pp. 1-12 (2019).

Chen et al., "Ultrasound shear wave elastography of breast lesions: correlation of anisotropy with clinical and histopathological findings," Cancer Imaging, vol. 18, No. 11, pp. 1-11 (2018).

Zahran et al., "Ultrasound elastography: How can it help in differentiating breast lesions?" The Egyptian Journal of Radiology and Nuclear Medicine, vol. 49, pp. 1-10 (2018).

Youk et al., "Shear-wave elastography in breast ultrasonography: the state of the art," Ultrasonography, vol. 36, No. 4, pp. 300-309 (Oct. 2017).

Selzo et al., "On the Quantitative Potential of Viscoelastic Response (VisR) Ultrasound Using the One-Dimensional Mass-Spring-Damper Model," IEEE Trans Ultrason Ferroelectr Freq Control, vol. 63, No. 9, pp. 1-29 (Sep. 2016).

Skerl et al., "Anisotropy of solid breast lesions in 2D shear wave elastography is an indicator of malignancy," Academic Radiology, vol. 23, No. 1, pp. 1-32 (2016).

Giannotti et al., "Shear-wave elastography and greyscale assessment of palpable probably benign masses: is biopsy always required?" Br J Radiol, vol. 89, pp. 1-7 (2016).

Kuzmiak, "Breast Cancer Survivors: Does the Screening MRI Debate Continue?" Acad Radiol, vol. 22, pp. 1329-1330 (2015).

Barr et al., "Shear-Wave Elastography of the Breast: Value of a Quality Measure and Comparison with Strain Elastography," Radiology, vol. 000, No. 0, pp. 1-9 (2015).

Grajo et al., "Strain Elastography for Prediction of Breast Cancer Tumor Grades," J Ultrasound Med, vol. 33, pp. 129-134 (2014).

Selzo et al., "Viscoelastic Response (VisR) Imaging for Assessment of Viscoelasticity in Voigt Materials," IEEE Trans Ultrason Ferroelectr Freq Control, vol. 60, No. 12, pp. 1-23 (Dec. 2013).

Cole et al., "Assessing the Standalone Sensitivity of Computer-aided Detection (CADe) with Cancer Cases from the Digital Mammographic Imaging Screening Trial (DMIST)," AJR Am J Roentgenol., vol. 199, No. 3, pp. 1-20 (2012).

Berg et al., "Detection of Breast Cancer with Addition of Annual Screening Ultrasound or a Single Screening MRI to Mammography in Women with Elevated Breast Cancer Risk," JAMA, vol. 307, No. 13, pp. 1-18 (Apr. 4, 2012).

(56) References Cited

OTHER PUBLICATIONS

Qiu et al., "Ultrasonic Viscoelasticity Imaging of Nonpalpable Breast Tumors: Preliminary Results," Acad Radiol, vol. 15, No. 12, pp. 1-17 (Dec. 2008).
Pinton et al., "Rapid Tracking of Small Displacements with Ultrasound," IEEE Transactions on Ultrasonics, Ferroelectrics, and Frequency Control, vol. 53 No. 6, pp. 1103-1117 (Jun. 2006).
Sinkus et al., "Imaging Anisotropic and Viscous Properties of Breast Tissue by Magnetic Resonance-Elastography," Magnetic Resonance in Medicine, vol. 53, pp. 372-387 (2005).
Palmeri et al., "A Finite-Element Method Model of Soft Tissue Response to Impulsive Acourstic Radiation Force," Transactions on Ultrasonics, Ferroelectrics, and Frequency Control, vol. 52, Issue 10, Oct. 2005, IEEE, pp. 1699-1712.
Rouze et al., "Finite Element Modeling of Impulsive Excitation and Shear Wave Propagation in an Incompressible, Transversely Isotropic Medium," Journal of Biomechanics, vol. 46, Issue 16, Nov. 2013, 18 pages.
Wang, Michael, et al., "Imaging Transverse Isotropic Properties of Muscle by Monitoring Acoustic Radiation Force Induced Shear Waves Using a 2-D Matrix Ultrasound Array," IEEE Transactions on Medical Imaging, vol. 32, Issue 9, Sep. 2013, pp. 1671-1684.
International Preliminary Report on Patentability for International Patent Application No. PCT/US2017/032745, dated Nov. 22, 2018, 18 pages.
International Search Report and Written Opinion for International Patent Application No. PCT/US2017/032745, dated Aug. 8, 2017, 23 pages.
Commonly-assigned, Co-pending U.S. Appl. No. 17/204,919 for "Quantitative Viscoelastic Response (QVISR) Ultrasound," (Unpublished, filed Mar. 17, 2021).
Hossain et al., "Improvement in Inclusion Contrast-to-Noise Ratio for Low-Displacement Acoustic Radiation Force (ARF) Elasticity Imaging Using a 3D Kernel Blind-Source Separation (BSS) Based Displacement Estimator," 2019 IEEE International Ultrasonics Symposium (IUS), pp. 1395-1398 (Oct. 2019).
Yokoyama et al., "Double-profile intersection (DoPIo) elastography: a new approach to quantifying tissue elasticity," 2019 IEEE International Ultrasonics Symposium (IUS), pp. 1-4 (Oct. 2019).
Hossain et al., "Evaluating Renal Transplant Status Using Viscoelastic Response (VISR) Ultrasound," Ultrasound in Med. & Biol., vol. 44, No. 8, pp. 1573-1584 (2018).
Moore et al., "In Vivo Viscoelastic Response (VisR) Ultrasound for Characterizing Mechanical Anisotrophy in Lower-Limb Skeletal Muscles of Boys with and without Duchenne Muscular Dystrophy," Ultrasound in Med Biol., vol. 44, No. 12, pp. 1-23 (Dec. 2018).
Hossain et al., "Acoustic Radiation Force Impulse-Induced Peak Displacements Reflect Degree of Anisotrophy in Transversely Isotropic Elastic Materials," IEEE Transactions on Ultrasonics, Ferroelectrics, and Frequency Control, vol. 64, No. 6, pp. 989-1001 (Jun. 2017).
Barr et al., "WFUMB Guidelines and Recommendations for Clinical Use of Ultrasound Elastography: Part 2: Breast," Ultrasound in Med. & Biol., vol. 41, No. 5, pp. 1148-1160 (2015).
Shiina et al., "WFUMB Guidelines and Recommendations for Clinical Use of Ultrasound Elastogrpahy: Part 1: Basic Principles and Terminology," Ultrasound in Med. & Biol., vol. 41, No. 5, pp. 1126-1147 (2015).
Ferraioli et al., "WFUMB Guidelines and Recommendations for Clinical Use of Ultrasound Elastography: Part 3: Liver," Ultrasound in Med & Biol., vol. 41, No. 5, pp. 1161-1179 (2015).
Czernuszewicz et al., "Experimental Validation of Displacement Underestimation in ARFI Ultrasound," Ultrason Imaging, vol. 35, No. 3, pp. 1-24 (Jul. 2013).
Dhanaliwala et al, "Assessing and improving acoustic radiation force image quality using a 1.5D transducer design," IEEE Trans Ultrason Ferroelectr Freq Control, vol. 59, No. 7, pp. 1-16 (Jul. 2012).
Nightingale, "Acoustic Radiation Force Impulse (ARFI) Imaging: a Review," Curr Med Imaging Rev., vol. 7, No. 4, pp. 1-24 (Nov. 1, 2011).
Pedregosa et al., "Scikit-learn: Machine Learning in Python," Journal of Medicine Learning Research, arXiv:1201.0490v4, vol. 12, pp. 1-6 (2011).
Ostrovsky et al., "Radiation force and shear motions in inhomogeneous media," The Journal of Acoustical Society of America, vol. 121, No. 1324 pp. 1-9 (2007).
Palmeri et al., "Ultrasonic Tracking of Acoustic Radiation Force-Induced Displacements in Homogeneous Media," IEEE Trans Ultrason Ferroelectr Freq Control, vol. 53, No. 7, pp. 1-24 (Jul. 2006).
Jensen et al., "Simulation of advanced ultrasound systems using Field II," In IEEE International Symposium on Biomedical Engineering, pp. 1-5 (2004).
Chen et al., "Quantifying elasticity and viscosity from measurement of shear wave speed dispersion," J. Acoust. Soc. Am., vol. 115, No. 6, pp. 2781-2785 (Jun. 2004).
Nightingale et al., "Sheav-wave Generation Using Acoustic Radiation Force: In Vivo and Ex Vivo Results," Ultrasound in Med. & Biol., vol. 29, No. 12, pp. 1-9 (2003).
Sandrin et al., "Transient Elastography: A New Noninvasive Method for Assessment of Hepatic Fibrosis," Ultrasound in Med. & Biol., vol. 29, No. 12, pp. 1-9 (2003).
McAleavey et al., "Estimates of Echo Correlation and Measurement Bias in Acoustic Radiation Force Impulse Imaging," IEEE Transactions on Ultrasonics, Ferroelectrics, and Frequency Control, vol. 50, No. 6, pp. 631-641 (Jun. 2003).
Nightingale et al., "Acoustic Radiation Force Impulse Imaging: In Vivo Demonstration of Clinical Feasibility," Ultrasound in Medicine and Biology, pp. 1-21 (Oct. 24, 2001).
Chan et al., "Active Contours Without Edges," IEEE Transactions on Image Processing, vol. 10, No. 2, pp. 266-277 (Feb. 2001).
Torr, "MLESAC: A New Robust Estimator with Application to Estimating Image Geometry," Computer Vision and Image Understanding, vol. 78, pp. 138-156 (2000).
Sarvazyan et al., "Shear Wave Elasticity Imaging: A New Ultrasonic Technology of Medical Diagnostics," Ultrasound in Med. & Biol., vol. 24, No. 9, pp. 1419-1435 (1998).
Walker et al., "A Fundamental Limit on Delay Estimation Using Partially Correlated Speckle Signals," IEEE Transactions on Ultrasonics, Ferroelectrics, and Frequency Control., vol. 42, No. 2, pp. 301-308 (Mar. 1995).
Ponnekanti et al., "Fundamental Mechanical Limitations on the Visualization of Elasticity Contrast in Elastography," Ultrasound in Med. & Biol., vol. 21, No. 4, pp. 533-543 (1995).
Jensen et al., "Calculation of Pressure Fields from Arbitrarily Shaped, Apodized, and Excited Ultrasound Transducers," IEEE Transactions on Ultrasonics, Ferroelectrics, and Frequency Control, vol. 39, No. 2, pp. 1-7 (1992).
Smith et al., "Properties of Acoustical Speckle in the Presence of Phase Aberration Part II: Correlation Lengths," Ultrasonic Imaging, pp. 29-51 (1988).
Trahey et al., "Properties of Acoustical Speckle in the Presence of Phase Aberration Part I: First Order Statistics," Ultrasonic Imaging, pp. 12-28 (1988).
Wagner et al., "Statistics of Speckle in Ultrasound B-Scans," IEEE Transactions on Sonics and Ultrasonics, vol. 30, No. 3, pp. 156-163 (May 1983).
Fritsch et al., "Monotone Piecewise Cubic Interpolation," Siam J. Numer. Anal., vol. 17, No. 2, pp. 238-246 (Apr. 1980).
Graustein, "Homogeneous Cartesian Coordinates, Linear Dependence of Points and Lines," Introduction to Higher Geometry, Chapter III, pp. 1-22 (1930).
Notice of Allowance for U.S. Appl. No. 17/150,612 (dated Mar. 7, 2022).

* cited by examiner

METHODS AND SYSTEMS FOR ASSESSING MATERIAL ANISOTROPY AND OTHER CHARACTERISTICS

RELATED APPLICATIONS

This application is a 35 U.S.C. § 371 national phase filing of International Application No. PCT/US2017/032745, filed May 15, 2017, which claims the benefit of provisional application Ser. No. 62/336,437, filed May 13, 2016, the disclosures of which are hereby incorporated herein by reference in their entireties.

This invention was made with government support under Grant Number NS074057 awarded by the National Institutes of Health. The government has certain rights in the invention.

BACKGROUND OF THE INVENTION

Acoustic radiation force (ARF)-based ultrasound imaging techniques are used to characterize the viscoelastic properties of tissue. Some tissues are anisotropic, meaning their viscoelastic properties exhibit directional dependence. The ability to measure and image the degree of anisotropy may be diagnostically relevant because some pathologies can alter tissue structure and thereby the degree of anisotropy. Thus, the ratio of maximum elasticity to minimum elasticity is a diagnostically relevant tool to detect tissue pathology.

Conventional methods measure relative elasticity by measuring shear wave velocity. This is difficult because it requires taking multiple frames of an image (e.g., a movie) and trying to measure the propagation speed of the shear wave as it radiates out from the point of force. This computationally expensive process is made more difficult by the fact that the propagating wave can be channeled by structures such as arteries and veins and can be reflected at boundaries of changing elasticity such as the surface of bones.

Thus, there is a need for improved methods of taking measurements of tissues and other materials, including methods and systems for assessing material anisotropy.

SUMMARY OF THE INVENTION

This technology utilizes acoustic radiation force based ultrasound or other force-producing techniques to excite tissue or materials and uses the resulting displacements, which can be measured quite accurately, to estimate the degree of anisotropy of the tissue or material. The technology utilizes a standard ultrasound scanner and a one-dimensional or two-dimensional ultrasound transducer to perform these measurements by taking the ratio of the displacements in two directions. The degree of anisotropy may be relevant as a diagnostic metric for applications in imaging skeletal muscle, kidney, and cardiac muscle, all of which are known to be anisotropic, as well as other organ systems. To date, this technology has been simulated using finite element analysis in anisotropic material models with varying degrees of anisotropy, and has been clinically demonstrated in human muscle and kidney tissues.

We have previously shown that ARF-induced displacements allow for point measurements of degree of anisotropy, using finite element simulation. However, to make these measurements with a linear array transducer requires a 90 degree rotation of the imaging transducer or the sample, potentially leading to misalignment. Alternatively, we have demonstrated the feasibility of creating images of degree of anisotropy using ARF-induced displacements produced by a simulated two-dimensional (2D) matrix array transducer. With a 2D transducer, rotation is not needed. Other transducer geometries, such as a row-column design, would also support such anisotropy measurements without transducer rotation.

According to one aspect of the subject matter described herein, a method for assessing material anisotropy includes: applying a first force to a material sample and taking a first measurement, the first force having a direction, having a coronal plane normal to the direction of the force, and having an oval or other profile with long and short axes within the coronal plane, the long axis being oriented in a first direction within the coronal plane; applying a second force to the material sample and taking a second measurement, the second force having a direction, having a coronal plane normal to the direction of the force, and having an oval or other profile with long and short axes within the coronal plane, the long axis being oriented in a second direction within the coronal plane different from the first direction of the first force; and calculating a material anisotropy based on the first and second measurements, wherein the first force and the second force are applied in any order.

In one embodiment, the angle difference between the first direction and the second direction is 90 degrees.

In one embodiment, the angle difference between the first direction and the second direction is an angle other than 90 degrees.

In one embodiment, the first and second measurements comprise measurements of displacement, measurements of relaxation time constant for constant stress (Tau), measurements of recovery time, measurements of strain, measurements of elasticity, or measurements of viscosity.

In one embodiment, the material sample comprises a tissue sample.

In one embodiment, calculating a material anisotropy based on the first and second measurements comprises calculating the material anisotropy based on a ratio of the larger of two measurements to the smaller of two measurements.

In one embodiment, calculating a material anisotropy comprises calculating an elasticity anisotropy.

In one embodiment, calculating a material anisotropy comprises calculating a viscosity anisotropy.

In one embodiment, the coronal plane is at a focal depth within the material sample.

In one embodiment, the direction of anisotropy of the material is known and wherein the first force has an orientation at a known angle relative to the direction of anisotropy of the material.

In one embodiment, the direction of anisotropy of the material is unknown and wherein the method further comprises sweeping an angle of orientation of a long axis of force within the coronal plane until two different measurements are taken at a known difference in angle of orientation, and using the two different measurements and known difference in angle of orientation to calculate the material anisotropy.

In one embodiment, the direction of anisotropy of the material is unknown and wherein the method further comprises sweeping an angle of orientation of a long axis of force within the coronal plane until maximum and minimum measurements are taken, and using the maximum and minimum measurements to calculate the material anisotropy.

In one embodiment, at least one of the forces is applied using a mechanical indenter.

In one embodiment, at least one of the forces is applied using a magnetic field.

In one embodiment, at least one of the forces is applied using an acoustic radiation force.

In one embodiment, the at least one force is applied using an ultrasound transducer.

In one embodiment, the first force is applied at a first focal depth, wherein the second force is applied at a second focal depth, and wherein the first focal depth is the same as the second focal depth.

In one embodiment, the first force is applied at a first focal depth, wherein the second force is applied at a second focal depth, and wherein the first focal depth is different than the second focal depth.

In one embodiment, the transducer's position and orientation are the same during application of the first force and the second force. (I.e., the position and orientation of the transducer does not change between application of the first force and application of the second force.)

In one embodiment, the ultrasound transducer comprises a lens.

In one embodiment, the ultrasound transducer comprises a plurality of emitter elements.

In one embodiment, the elements are arranged in a one-dimensional configuration.

In one embodiment, the one-dimensional configuration comprises a linear array.

In one embodiment, the direction of the long axis of the first force is controlled by rotation of the transducer about an axis normal to the coronal plane.

In one embodiment, the elements are arranged in a two-dimensional configuration.

In one embodiment, the two-dimensional configuration comprises one of: a fully-populated grid; a sparsely-populated grid; a checkerboard pattern; a tic-tac-toe board pattern; a cross shape; a square or rectangle; a circle, oval, or ellipse; or combinations of the above.

In one embodiment, the direction of the long axis of the first force is controlled without rotation of the transducer about an axis normal to the coronal plane.

In one embodiment, at least one of the measurements is taken using ultrasound.

In one embodiment, at least one of the measurements is taken using magnetic resonance imaging (MRI).

In one embodiment, at least one of the measurements is taken using an optical method. In one embodiment, the optical method comprises optical coherence tomography (OCT).

In one embodiment, at least one of the measurements is taken using a mechanical micrometer.

In one embodiment, at least one of the measurements is taken using an optical microscope or other optical imaging or video method.

In one embodiment, the step of applying the first force and taking the first measurement is performed a plurality of times to produce a plurality of first measurements, wherein the step of applying the second force and taking the second measurement is applied a plurality of times, and wherein a material characteristic is calculated based on the plurality of first and second measurements. Examples of characteristics that may be so calculated include, but are not limited to, viscosity anisotropy, elasticity anisotropy, Tau values, and other metrics.

According to another aspect of the subject matter described herein, a system for assessing material anisotropy is adapted to: apply a first force to a material sample and take a first measurement, the first force having a direction, having a coronal plane normal to the direction of the force, and having an oval or other profile with long and short axes within the coronal plane, the long axis being oriented in a first direction within the coronal plane; apply a second force to the material sample and take a second measurement, the second force having a direction, having a coronal plane normal to the direction of the force, and having an oval or other profile with long and short axes within the coronal plane, the long axis being oriented in a second direction within the coronal plane different from the first direction of the first force; and calculate a material anisotropy based on the first and second measurements, wherein the first force and the second force are applied in any order.

According to another aspect of the subject matter described herein, a system for assessing material anisotropy comprises: means for applying a first force to a material sample and taking a first measurement, the first force having a direction, having a coronal plane normal to the direction of the force, and having an oval or other profile with long and short axes within the coronal plane, the long axis being oriented in a first direction within the coronal plane; means for applying a second force to the material sample and taking a second measurement, the second force having a direction, having a coronal plane normal to the direction of the force, and having an oval or other profile with long and short axes within the coronal plane, the long axis being oriented in a second direction within the coronal plane different from the first direction of the first force; and means for calculating a material anisotropy based on the first and second measurements, wherein the first force and the second force are applied in any order.

According to another aspect of the subject matter described herein, a system for assessing a material anisotropy comprises: a force applying module operable to apply, to a material sample, a plurality of forces having a direction and a coronal plane normal to the direction of the force; a measurement module operable to measure, for each of the plurality of forces, a displacement of the material caused by the force; and a calculation module operable to calculate a material anisotropy based on the plurality of measured material displacements. The plurality of forces may comprise one or more forces in each of two or more directions. In one embodiment, for example, a force having one profile or orientation may be applied one or more times, and a force having another profile or orientation may be applied one or more times. In another embodiment, a force having a particular profile or orientation may be applied multiple times in a manner designed to detect, accommodate, or avoid a resonant property of the tissue.

According to another aspect of the subject matter described herein, a non-transitory computer readable medium storing software instructions that when executed by one or more processors of a system for assessing material anisotropy cause the system to: apply a first force to a material sample and take a first measurement, the first force having a direction, having a coronal plane normal to the direction of the force, and having an oval or other profile with long and short axes within the coronal plane, the long axis being oriented in a first direction within the coronal plane; apply a second force to the material sample and take a second measurement, the second force having a direction, having a coronal plane normal to the direction of the force, and having an oval or other profile with long and short axes within the coronal plane, the long axis being oriented in a second direction within the coronal plane different from the first direction of the first force; and calculate a material anisotropy based on the first and second measurements, wherein the first force and the second force are applied in any order.

According to another aspect of the subject matter described herein, a computer program comprising instructions which, when executed by at least one processor, cause the at least one processor to carry out any of the methods described herein.

According to another aspect of the subject matter described herein, a method for taking a material measurement comprises: applying a first force to a material sample and taking a first measurement, the first force having a direction, having a coronal plane normal to the direction of the force, and having an oval or other profile with long and short axes within the coronal plane, the long axis being oriented in a first direction within the coronal plane; applying a second force to the material sample and taking a second measurement, the second force having a direction, having a coronal plane normal to the direction of the force, and having a circular or other profile with equi-length axes (axes having equivalent length) within the coronal plane; and normalizing the first measurement using the second measurement to produce a first normalized measurement, wherein the first force and the second force are applied in any order.

In one embodiment, the angle difference between the first direction and the second direction is 90 degrees.

In one embodiment, the angle difference between the first direction and the second direction is an angle other than 90 degrees.

In one embodiment, the first and second measurements comprise: measurements of displacement; measurements of relaxation time constant for constant stress (Tau); measurements of recovery time; measurements of strain; measurements of elasticity; or measurements of viscosity.

In one embodiment, the material sample comprises a tissue sample.

In one embodiment, the method further comprises: applying a third force to a material sample and taking a third measurement, the third force having a direction, having a coronal plane normal to the direction of the force, and having an oval or other profile with long and short axes within the coronal plane, the long axis being oriented in a second direction within the coronal plane different from the first direction of the first force; and normalizing the third measurement using the second measurement to produce a second normalized measurement, wherein the first force, the second force, and the third force are applied in any order.

In one embodiment, the method further comprises: applying a third force to a material sample and taking a third measurement, the third force having a direction, having a coronal plane normal to the direction of the force, and having an oval or other profile with long and short axes within the coronal plane, the long axis being oriented in a second direction within the coronal plane different from the first direction of the first force; and applying a fourth force to the material sample and taking a fourth measurement, the fourth force having a direction, having a coronal plane normal to the direction of the force, and having a circular or other profile with equi-length axes within the coronal plane; and normalizing the third measurement using the fourth measurement to produce a second normalized measurement, wherein the first force, the second force, the third force, and the fourth force are applied in any order.

In one embodiment, the method further comprises calculating a material anisotropy based on the first normalized measurement and the second normalized measurement.

In one embodiment, calculating a material anisotropy based on the first and second measurements comprises calculating the material anisotropy based on a ratio of the larger of two measurements to the smaller of two measurements.

In one embodiment, calculating a material anisotropy comprises calculating an elasticity anisotropy.

In one embodiment, calculating a material anisotropy comprises calculating a viscosity anisotropy.

In one embodiment, the coronal plane is at a focal depth within the material sample.

In one embodiment, the direction of anisotropy of the material is known and wherein the first force has an orientation at a known angle relative to the direction of anisotropy of the material.

In one embodiment, the direction of anisotropy of the material is unknown and wherein the method further comprises sweeping an angle of orientation of a long axis of force within the coronal plane until two different measurements are taken at a known difference in angle of orientation, and using the two different measurements and known difference in angle of orientation to calculate the material anisotropy.

In one embodiment, the direction of anisotropy of the material is unknown and wherein the method further comprises sweeping an angle of orientation of a long axis of force within the coronal plane until maximum and minimum measurements are taken, and using the maximum and minimum measurements to calculate the material anisotropy.

In one embodiment, at least one of the forces is applied using a mechanical indenter.

In one embodiment, at least one of the forces is applied using a magnetic field.

In one embodiment, at least one of the forces is applied using an acoustic radiation force.

In one embodiment, the at least one force is applied using an ultrasound transducer.

In one embodiment, the first force is applied at a first focal depth, wherein the second force is applied at a second focal depth, and wherein the first focal depth is the same as the second focal depth.

In one embodiment, the first force is applied at a first focal depth, wherein the second force is applied at a second focal depth, and wherein the first focal depth is different than the second focal depth.

In one embodiment, the transducer's position and orientation are the same during application of the first force and the second force. (I.e., the position and orientation of the transducer does not change between application of the first force and application of the second force.)

In one embodiment, the ultrasound transducer comprises a lens.

In one embodiment, the ultrasound transducer comprises a plurality of emitter elements.

In one embodiment, the elements are arranged in a one-dimensional configuration.

In one embodiment, the one-dimensional configuration comprises a linear array.

In one embodiment, the direction of the long axis of the first force is controlled by rotation of the transducer about an axis normal to the coronal plane.

In one embodiment, the elements are arranged in a two-dimensional configuration.

In one embodiment, the two-dimensional configuration comprises one of: a fully-populated grid; a sparsely-populated grid; a checkerboard pattern; a tic-tac-toe board pattern; a cross shape; a square or rectangle; a circle, oval, or ellipse; or combinations of the above.

In one embodiment, the direction of the long axis of the first force is controlled without rotation of the transducer about an axis normal to the coronal plane.

In one embodiment, at least one of the measurements is taken using ultrasound.

In one embodiment, at least one of the measurements is taken using MRI.

In one embodiment, at least one of the measurements is taken using an optical method. In one embodiment, the optical method comprises OCT.

In one embodiment, at least one of the measurements is taken using a mechanical micrometer.

In one embodiment, at least one of the measurements is taken using an optical microscope.

In one embodiment, the step of applying the first force and taking the first measurement is performed a plurality of times to produce a plurality of first measurements, wherein the step of applying the second force and taking the second measurement is applied a plurality of times, and wherein a material viscosity anisotropy is calculated based on the plurality of first and second measurements.

According to another aspect of the subject matter described herein, a system for taking a material measurement is adapted to: apply a first force to a material sample and take a first measurement, the first force having a direction, having a coronal plane normal to the direction of the force, and having an oval or other profile with long and short axes within the coronal plane, the long axis being oriented in a first direction within the coronal plane; apply a second force to the material sample and take a second measurement, the second force having a direction, having a coronal plane normal to the direction of the force, and having a circular or other profile with equi-length axes within the coronal plane; and normalize the first measurement using the second measurement to produce a first normalized measurement, wherein the first force and the second force are applied in any order.

According to another aspect of the subject matter described herein, a system for taking a material measurement comprises: means for applying a first force to a material sample and taking a first measurement, the first force having a direction, having a coronal plane normal to the direction of the force, and having an oval or other profile with long and short axes within the coronal plane, the long axis being oriented in a first direction within the coronal plane; means for applying a second force to the material sample and taking a second measurement, the second force having a direction, having a coronal plane normal to the direction of the force, and having a circular or other profile with equi-length axes within the coronal plane; and means for normalizing the first measurement using the second measurement to produce a first normalized measurement, wherein the first force and the second force are applied in any order.

According to another aspect of the subject matter described herein, a system for taking a material measurement comprises: a force applying module operable to apply, to a material sample, a plurality of forces having a direction and a coronal plane normal to the direction of the force; a measurement module operable to take, for each of the plurality of forces, a material measurement; and a calculation module operable to normalize one of the plurality of measurements using another of the plurality of measurements to produce a normalized measurement.

According to another aspect of the subject matter described herein, a non-transitory computer readable medium storing software instructions that when executed by one or more processors of a system for taking a material measurement cause the system to: apply a first force to a material sample and take a first measurement, the first force having a direction, having a coronal plane normal to the direction of the force, and having an oval or other profile with long and short axes within the coronal plane, the long axis being oriented in a first direction within the coronal plane; apply a second force to the material sample and take a second measurement, the second force having a direction, having a coronal plane normal to the direction of the force, and having a circular or other profile with equi-length axes within the coronal plane; and normalize the first measurement using the second measurement to produce a first normalized measurement, wherein the first force and the second force are applied in any order.

According to another aspect of the subject matter described herein, a computer program comprising instructions which, when executed by at least one processor, cause the at least one processor to carry out any of the methods described herein.

According to another aspect of the subject matter described herein, a method for taking a material measurement comprises: applying a first force to a material sample and taking a first measurement, the first force having a direction, having a coronal plane normal to the direction of the force, and having a circular or other profile with equi-length axes within the coronal plane; applying a second force to the material sample and taking a second measurement, the second force having a direction, having a coronal plane normal to the direction of the force, and having a circular or other profile with equi-length axes within the coronal plane; and assessing a material property based on a difference between the first measurement and the second measurement, wherein the first force and the second force are applied in any order.

In one embodiment, the angle difference between the first direction and the second direction is 90 degrees.

In one embodiment, the angle difference between the first direction and the second direction is an angle other than 90 degrees.

In one embodiment, the first and second measurements comprise: measurements of displacement; measurements of relaxation time constant for constant stress (Tau); measurements of recovery time; measurements of strain; measurements of elasticity; or measurements of viscosity.

In one embodiment, the material sample comprises a tissue sample.

In one embodiment, assessing a material property based on a difference between the first measurement and the second measurement comprises determining whether a difference between the first and second measurements exceeds a threshold.

In one embodiment, the method comprises, in response to determining that the difference between the first and second measurements exceeds the threshold, determining a change in tissue pathology.

According to another aspect of the subject matter described herein, a system for taking a material measurement is adapted to: apply a first force to a material sample and take a first measurement, the first force having a direction, having a coronal plane normal to the direction of the force, and having a circular or other profile with equi-length axes within the coronal plane; apply a second force to the material sample and take a second measurement, the second force having a direction, having a coronal plane normal to the direction of the force, and having a circular or other profile with equi-length axes within the coronal plane; and determine a material property based on a difference between the first measurement and the second measurement, wherein the first force and the second force are applied in any order.

According to another aspect of the subject matter described herein, a system for taking a material measurement comprises: means for applying a first force to a material sample and taking a first measurement, the first force having a direction, having a coronal plane normal to the direction of the force, and having a circular or other profile with equi-length axes within the coronal plane; means for applying a second force to the material sample and taking a second measurement, the second force having a direction, having a coronal plane normal to the direction of the force, and having a circular or other profile with equi-length axes within the coronal plane; and means for assessing a material property based on a difference between the first measurement and the second measurement, wherein the first force and the second force are applied in any order.

According to another aspect of the subject matter described herein, a system for taking a material measurement comprises: a force applying module operable to apply, to a material sample, a plurality of forces having a direction, having a coronal plane normal to the direction of the force, and having a circular or other profile with equi-length axes within the coronal plane; a measurement module operable to take, for each of the plurality of forces, a material measurement; and a calculation module operable to determine a material property based on the plurality of material measurements.

According to another aspect of the subject matter described herein, a non-transitory computer readable medium storing software instructions that when executed by one or more processors of a system for taking a material measurement cause the system to: apply a first force to a material sample and take a first measurement, the first force having a direction, having a coronal plane normal to the direction of the force, and having a circular or other profile with equi-length axes within the coronal plane; apply a second force to the material sample and take a second measurement, the second force having a direction, having a coronal plane normal to the direction of the force, and having a circular or other profile with equi-length axes within the coronal plane; and determine a material property based on a difference between the first measurement and the second measurement, wherein the first force and the second force are applied in any order.

According to another aspect of the subject matter described herein, a computer program comprising instructions which, when executed by at least one processor, cause the at least one processor to carry out any of the methods described herein.

According to another aspect of the subject matter described herein, a system for taking a material measurement comprises: a force producing unit for applying a force to a material sample; a measuring device for taking a material measurement corresponding to the forces; one or more processors; and memory storing instructions executable by the one or more processors, whereby the system is operable to determine a material property based on a plurality of applied forces and their corresponding plurality of material measurements.

In one embodiment, at least one of the material measurements comprise: a measurement of displacement; a measurement of relaxation time constant for constant stress (Tau); a measurement of recovery time; a measurement of strain; a measurement of elasticity; or a measurement of viscosity.

In one embodiment, the material sample comprises a tissue sample.

In one embodiment, via execution of instructions by the one or more processors, the system is operable to: apply a first force to a material sample and take a first measurement, the first force having a direction, having a coronal plane normal to the direction of the force, and having an oval or other profile with long and short axes within the coronal plane, the long axis being oriented in a first direction within the coronal plane; apply a second force to the material sample and take a second measurement, the second force having a direction, having a coronal plane normal to the direction of the force, and having an oval or other profile with long and short axes within the coronal plane, the long axis being oriented in a second direction within the coronal plane different from the first direction of the first force; and calculate a material anisotropy based on the first and second measurements, wherein the first force and the second force are applied in any order.

In one embodiment, via execution of instructions by the one or more processors, the system is operable to: apply a first force to a material sample and take a first measurement, the first force having a direction, having a coronal plane normal to the direction of the force, and having an oval or other profile with long and short axes within the coronal plane, the long axis being oriented in a first direction within the coronal plane; apply a second force to the material sample and take a second measurement, the second force having a direction, having a coronal plane normal to the direction of the force, and having a circular or other profile with equi-length axes within the coronal plane; and normalize the first measurement using the second measurement to produce a first normalized measurement, wherein the first force and the second force are applied in any order.

In one embodiment, via execution of instructions by the one or more processors, the system is further operable to: apply a third force to a material sample and take a third measurement, the third force having a direction, having a coronal plane normal to the direction of the force, and having an oval or other profile with long and short axes within the coronal plane, the long axis being oriented in a second direction within the coronal plane different from the first direction of the first force; and normalize the third measurement using the second measurement to produce a second normalized measurement, wherein the first force, the second force, and the third force are applied in any order.

In one embodiment, via execution of instructions by the one or more processors, the system is further operable to: apply a third force to a material sample and take a third measurement, the third force having a direction, having a coronal plane normal to the direction of the force, and having an oval or other profile with long and short axes within the coronal plane, the long axis being oriented in a second direction within the coronal plane different from the first direction of the first force; and apply a fourth force to the material sample and take a fourth measurement, the fourth force having a direction, having a coronal plane normal to the direction of the force, and having a circular or other profile with equi-length axes within the coronal plane; and normalize the third measurement using the fourth measurement to produce a second normalized measurement, wherein the first force, the second force, the third force, and the fourth force are applied in any order.

In one embodiment, via execution of instructions by the one or more processors, the system is operable to: apply a first force to a material sample and take a first measurement, the first force having a direction, having a coronal plane normal to the direction of the force, and having a circular or other profile with equi-length axes within the coronal plane; apply a second force to the material sample and take a second measurement, the second force having a direction, having a coronal plane normal to the direction of the force, and having a circular or other profile with equi-length axes within the coronal plane; and determine a material property based on a difference between the first measurement and the second measurement, wherein the first force and the second force are applied in any order.

In one embodiment, determining a material property based on a difference between the first measurement and the second measurement comprises determining whether a difference between the first and second measurements exceeds a threshold.

In one embodiment, the material sample comprises a tissue sample and wherein, in response to determining that the difference between the first and second measurements exceeds a threshold, determining a change in tissue pathology.

In one embodiment, via execution of instructions by the one or more processors, the system is operable to calculate a material anisotropy based on the first normalized measurement and the second normalized measurement.

In one embodiment, calculating a material anisotropy comprises calculating an elasticity anisotropy.

In one embodiment, calculating a material anisotropy comprises calculating a viscosity anisotropy.

In one embodiment, the coronal plane is at a focal depth within the material sample.

In one embodiment, the direction of anisotropy of the material is known and wherein the first force has an orientation at a known angle relative to the direction of anisotropy of the material.

In one embodiment, the direction of anisotropy of the material is unknown and wherein, via execution of instructions by the one or more processors, the system is operable to sweep an angle of orientation of a long axis of force within the coronal plane until two different measurements are taken at a known difference in angle of orientation, and use the two different measurements and known difference in angle of orientation to calculate the material anisotropy.

In one embodiment, the direction of anisotropy of the material is unknown and wherein, via execution of instructions by the one or more processors, the system is operable to sweep an angle of orientation of a long axis of force within the coronal plane until maximum and minimum measurements are taken, and use the maximum and minimum measurements to calculate the material anisotropy.

In one embodiment, the force producing unit comprises a mechanical indenter.

In one embodiment, the force producing unit produces a magnetic field.

In one embodiment, the force producing unit comprises an ultrasound transducer.

In one embodiment, the first force is applied at a first focal depth, wherein the second force is applied at a second focal depth, and wherein the first focal depth is the same as the second focal depth.

In one embodiment, the first force is applied at a first focal depth, wherein the second force is applied at a second focal depth, and wherein the first focal depth is different than the second focal depth.

In one embodiment, the transducer's position and orientation are the same during application of the first force and the second force. (I.e., the position and orientation of the transducer does not change between application of the first force and application of the second force.)

In one embodiment, the ultrasound transducer comprises a lens.

In one embodiment, the ultrasound transducer comprises a plurality of emitter elements.

In one embodiment, the elements are arranged in a one-dimensional configuration.

In one embodiment, the one-dimensional configuration comprises a linear array.

In one embodiment, the ultrasound transducer produces a force having an oval or other profile with long and short axes within the coronal plane and wherein the direction of the long axis of the first force is controlled by rotation of the transducer about an axis normal to the coronal plane.

In one embodiment, the elements are arranged in a two-dimensional configuration.

In one embodiment, the two-dimensional configuration comprises one of: a fully-populated grid; a sparsely-populated grid; a checkerboard pattern; a tic-tac-toe board pattern; a cross shape; a square or rectangle; a circle, oval, or ellipse; or combinations of the above.

In one embodiment, the ultrasound transducer produces a force having an oval or other profile with long and short axes within the coronal plane and wherein the direction of the long axis of the first force is controlled without rotation of the transducer about an axis normal to the coronal plane.

In one embodiment, at least one of the measurements is taken using ultrasound.

In one embodiment, at least one of the measurements is taken using MRI.

In one embodiment, at least one of the measurements is taken using an optical method. In one embodiment, the optical method comprises OCT.

In one embodiment, at least one of the measurements is taken using a mechanical micrometer.

In one embodiment, at least one of the measurements is taken using an optical microscope.

In one embodiment, via execution of instructions by the one or more processors, the system is operable to: apply a first force and take a first measurement a plurality of times to produce a plurality of first measurements; apply a second force and take a second measurement a plurality of times to produce a plurality of second measurements; and calculate a material viscosity based on the plurality of first and second measurements.

Those skilled in the art will appreciate the scope of the present invention and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the invention, and together with the description serve to explain the principles of the invention.

Figure 3:
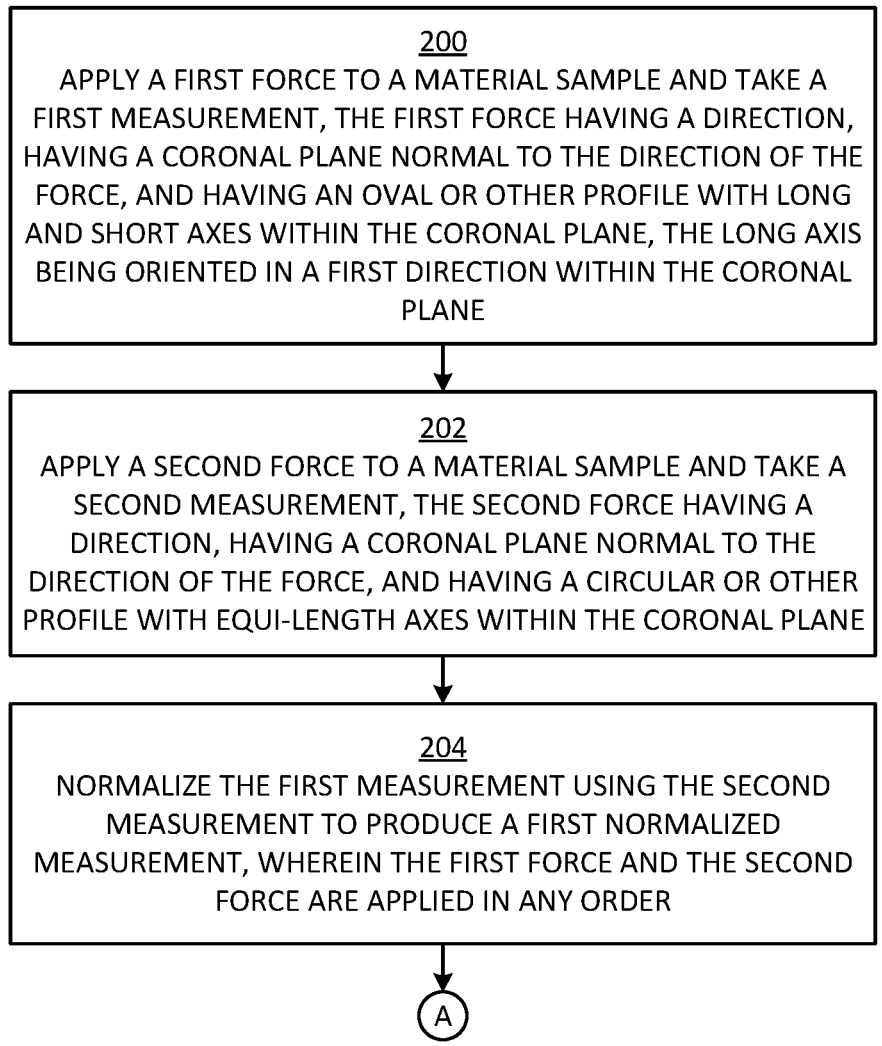
Figure 4:
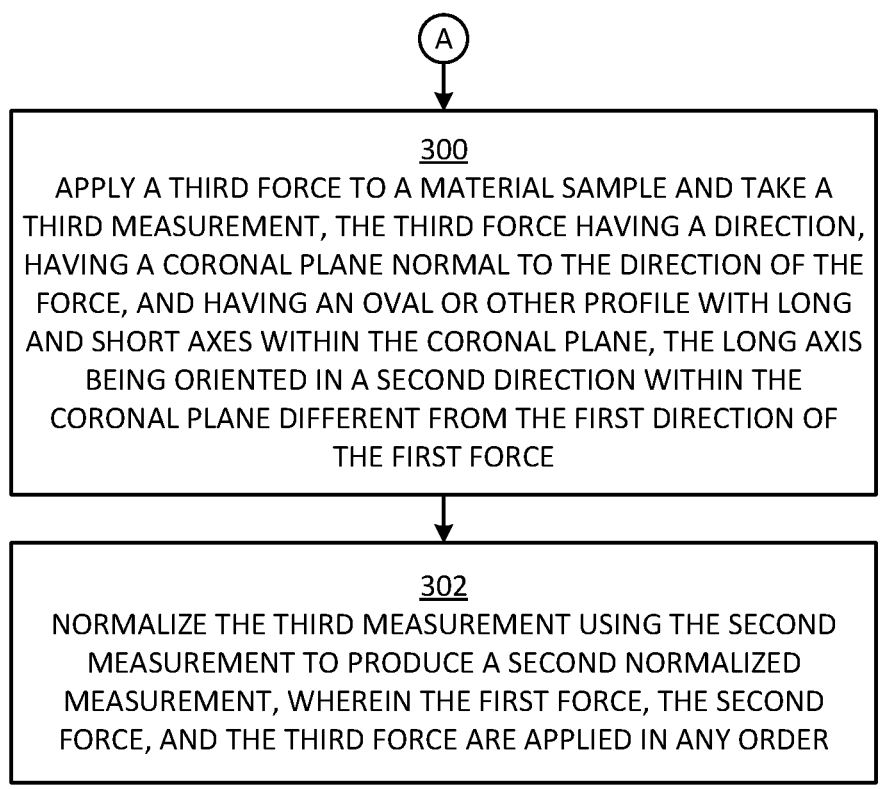
Figure 5:
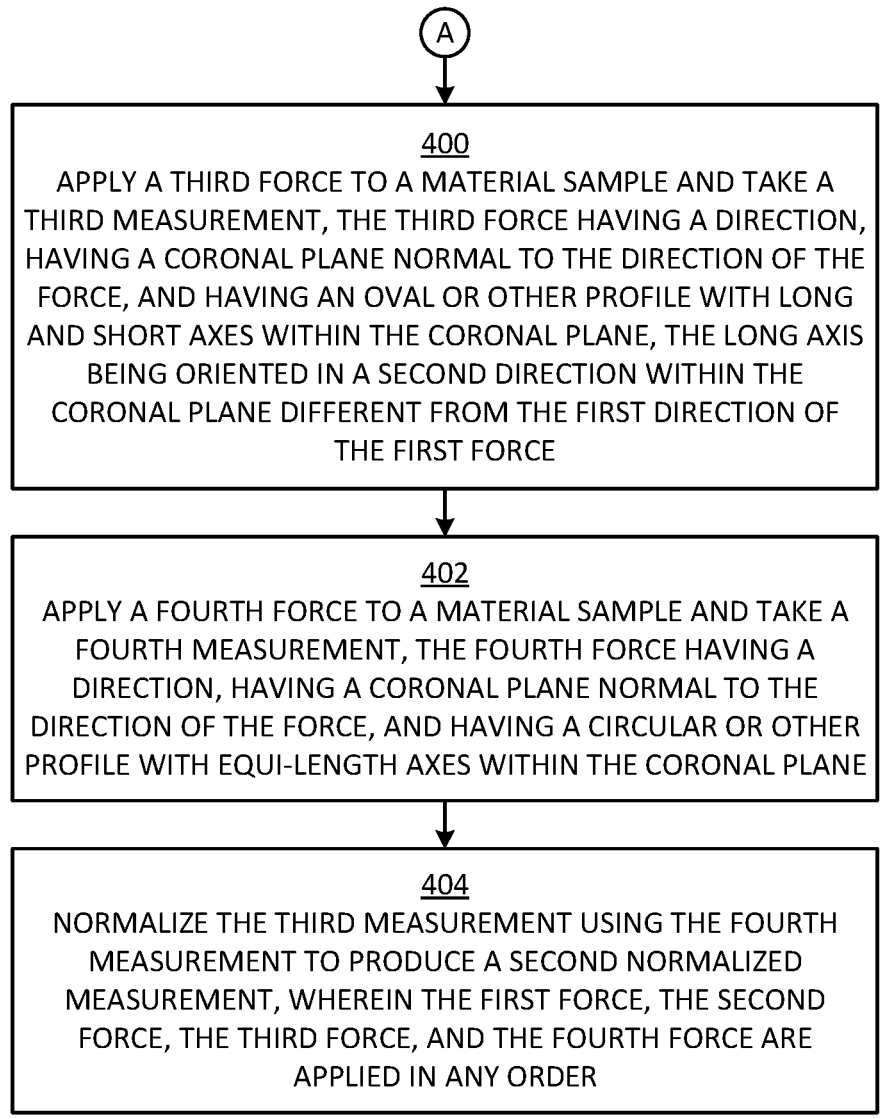

FIGS. 3, 4, and 5 illustrate flow charts showing portions of an exemplary process for taking a material measurement according to an embodiment of the subject matter described herein.

Figure 6:
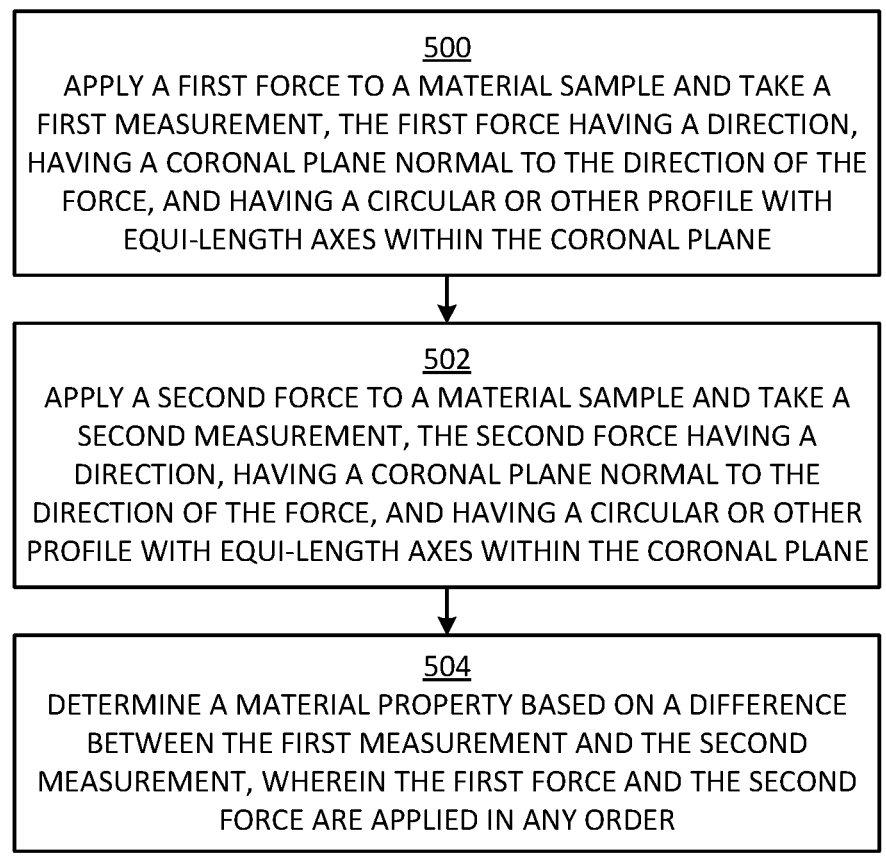

FIG. 6 illustrates a flow chart for an exemplary process for taking a material measurement according to an embodiment of the subject matter described herein.

Figure 7:
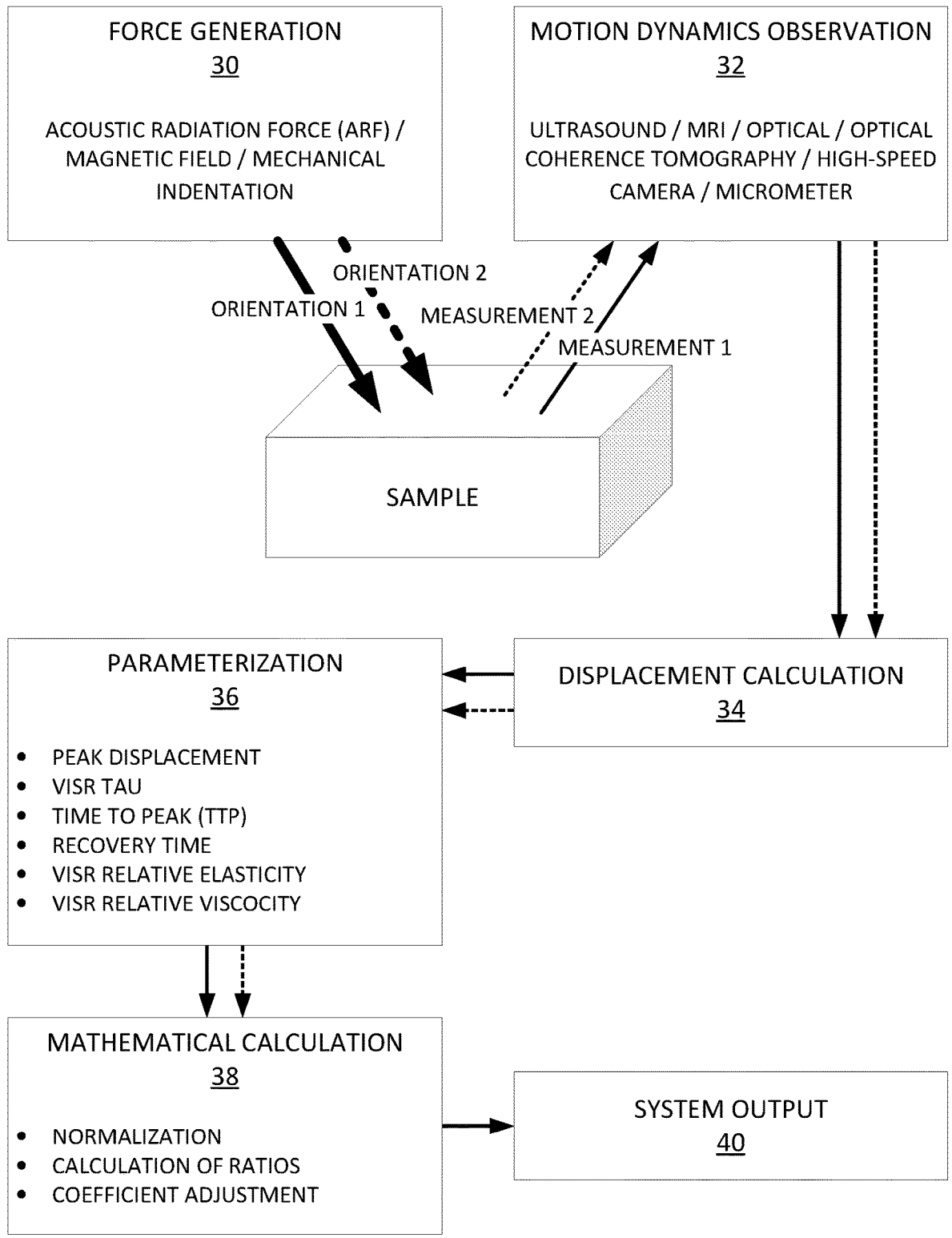

FIG. 7 is block diagram illustrating a system for taking a material measurement, which may include assessing material anisotropy, according to an embodiment of the subject matter described herein.

Figure 8A:
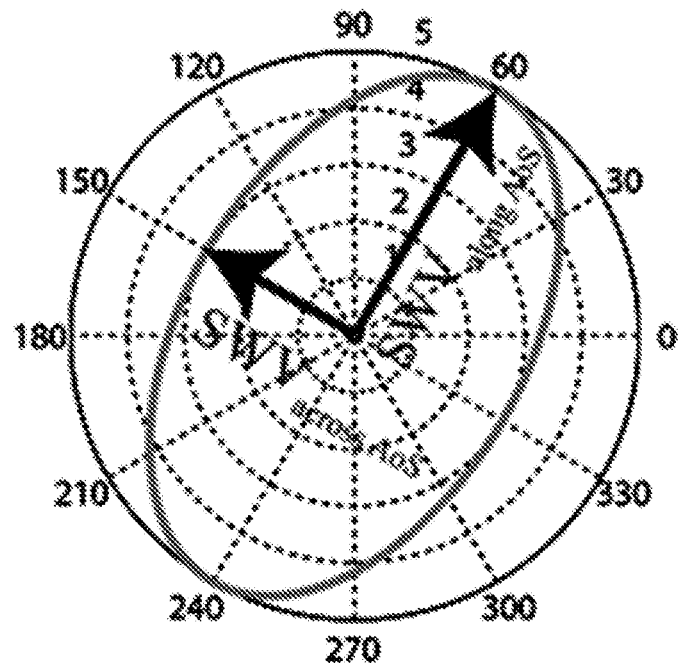

FIG. 8A shows the group velocity [$ms^{-1}$] of a shear wave travelling in a transversely isotropic (TI) material.

Figure 8B:
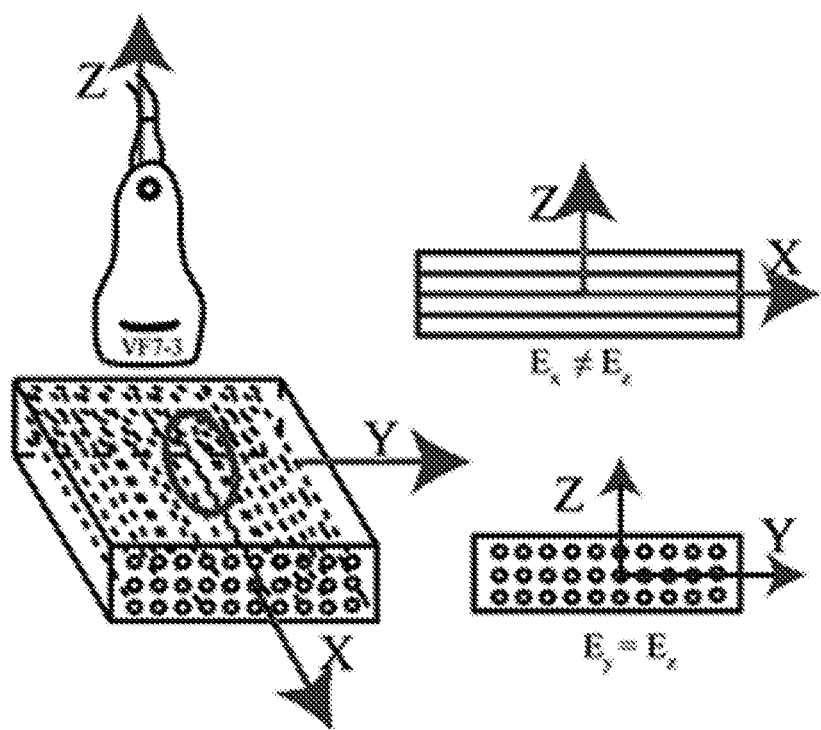
Figure 9A:
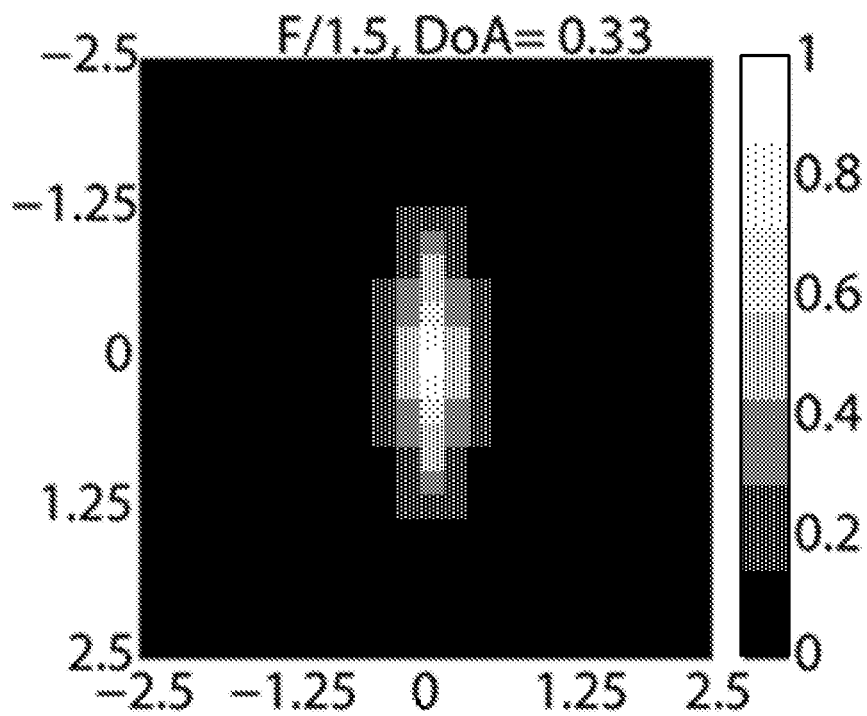
Figure 9B:
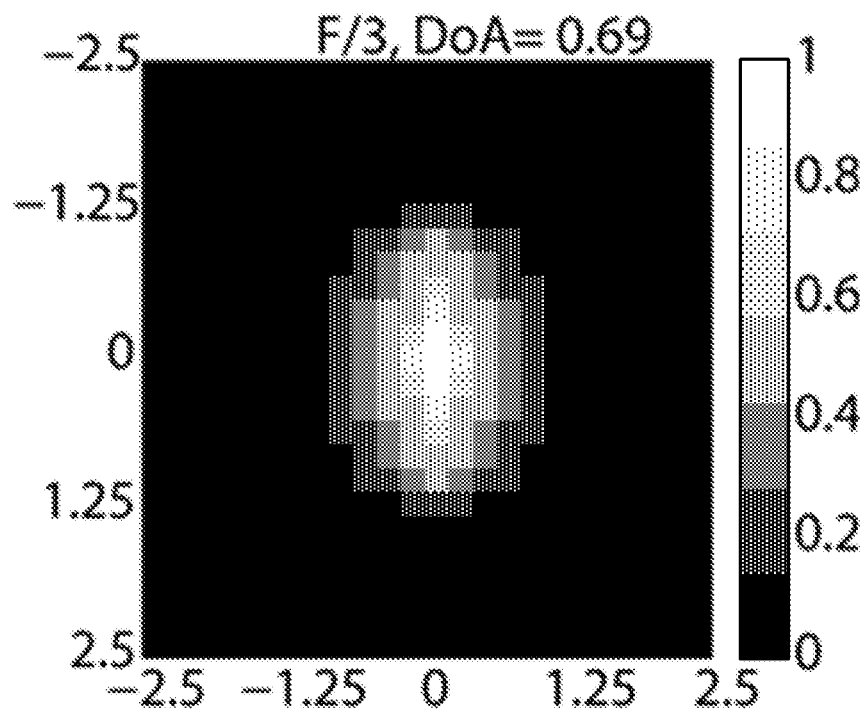
Figure 9C:
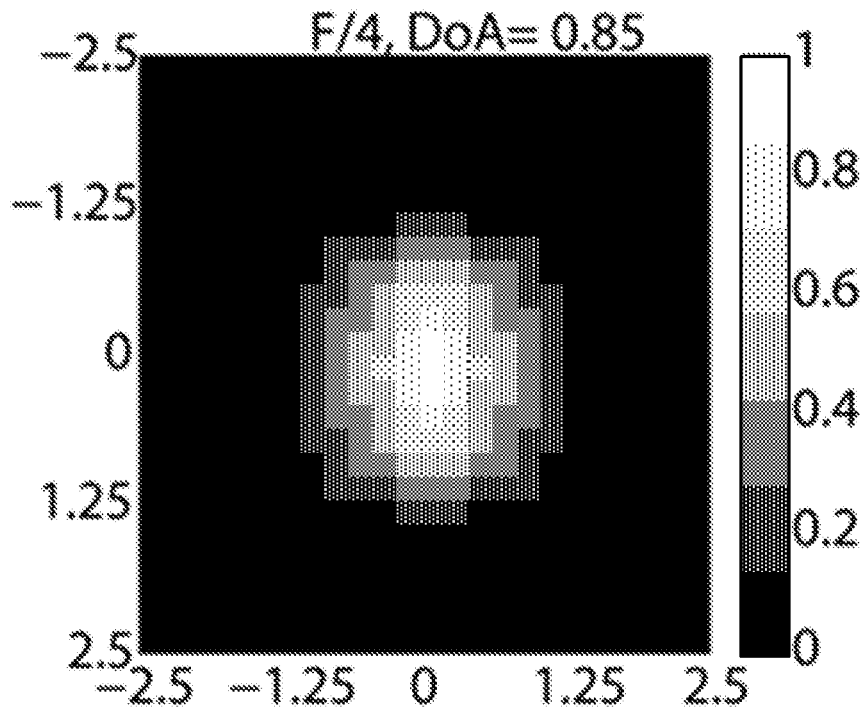
Figure 9D:
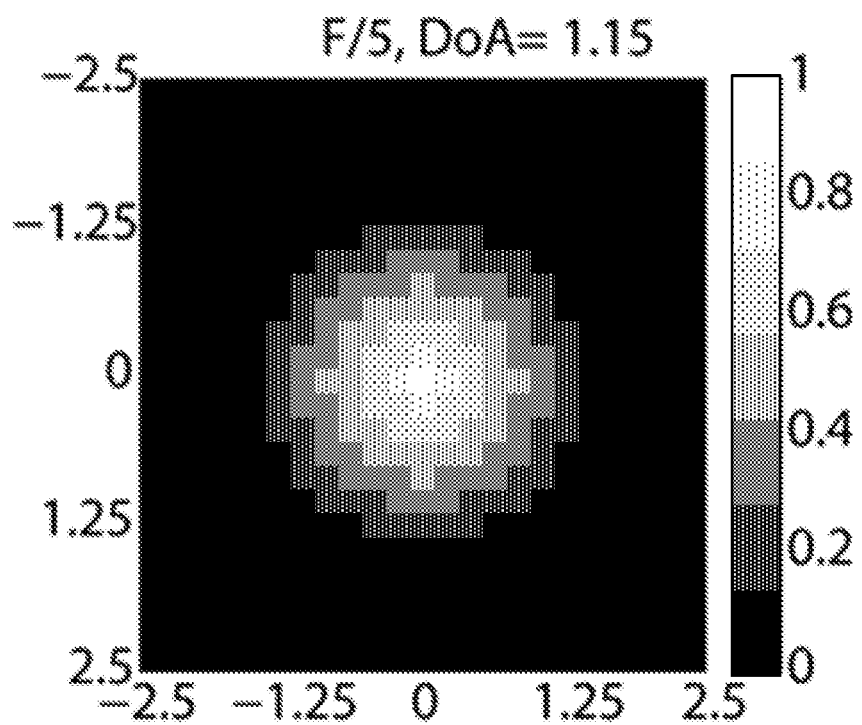

FIG. 8B shows the XYZ coordinate system used to describe the material's axis of symmetry (AoS) orientation with respect to the acoustic radiation force impulse (ARFI) excitation 2D point spread function (PSF).

FIGS. 9A through 9D show the spatial distribution of the ARFI-2D PSF in the lateral-elevational plane at the focal depth (36 mm) for focal configurations of F/1.5, 3, 4, and 5, respectively with their respective degree of asymmetry values.

Figure 10A:
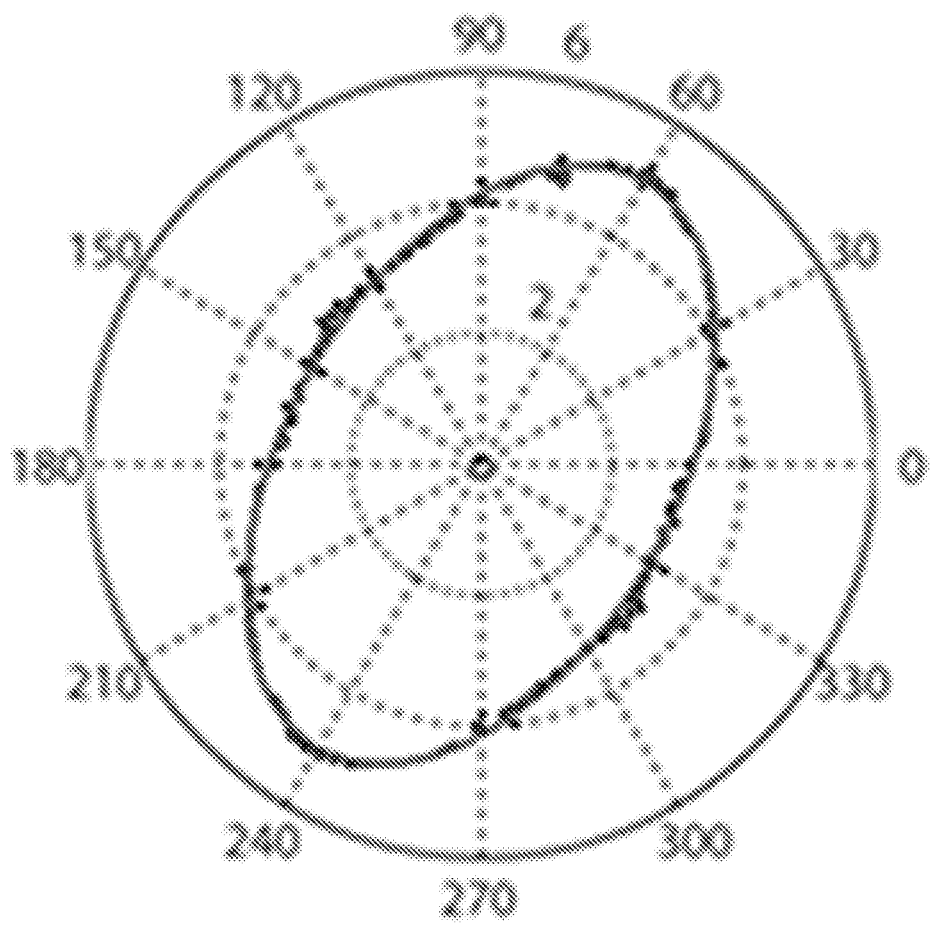

FIG. 10A shows elliptical shear wave propagation in a representative modeled TI material.

Figure 10B:
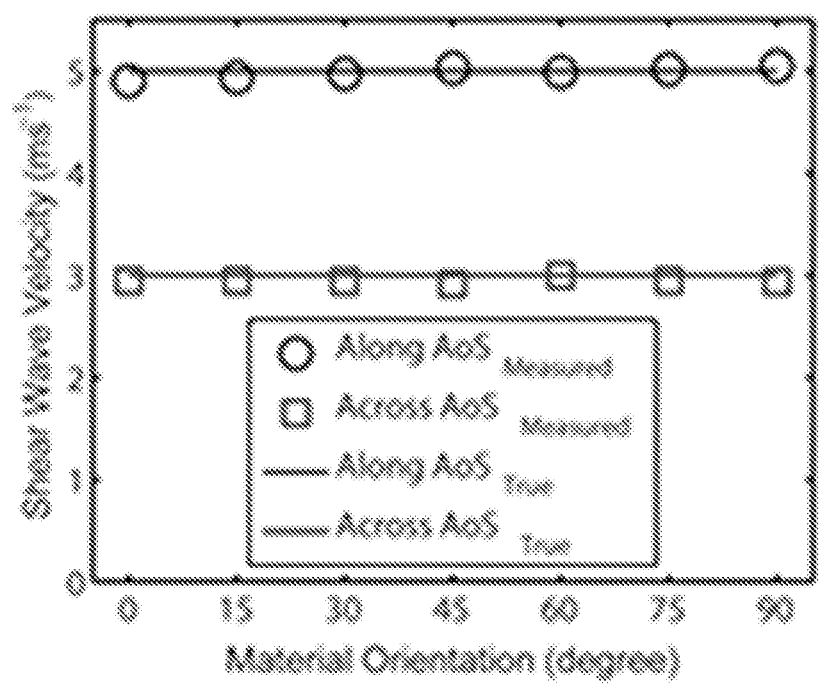

FIG. 10B shows both expected (True) and measured (Measured) shear wave velocities (SWVs) along and across the AoS for the seven material-PSF orientations.

Figure 10C:
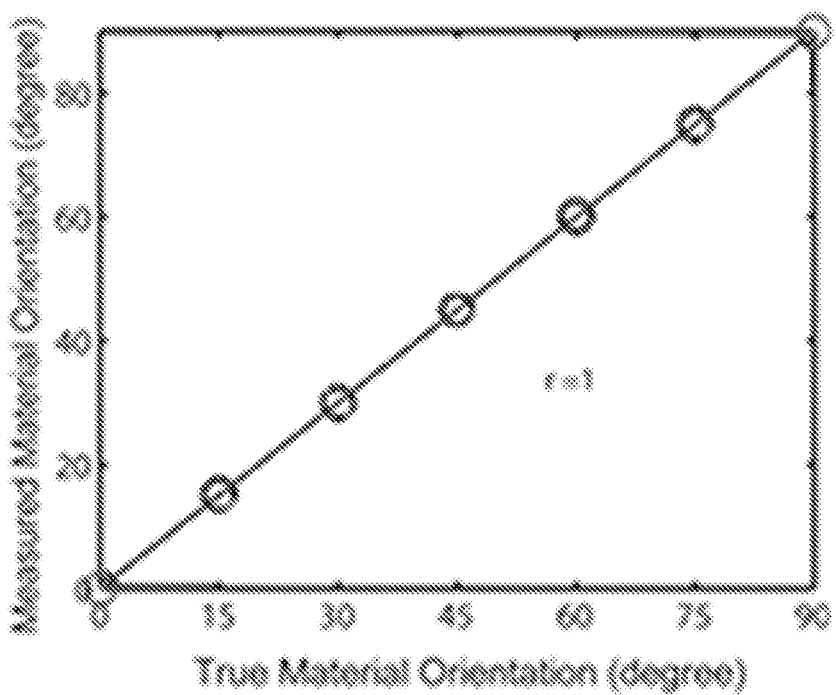

FIG. 10C shows a plot of measured AoS orientations from the fitted ellipse versus true material AoS orientations.

Figure 11A:
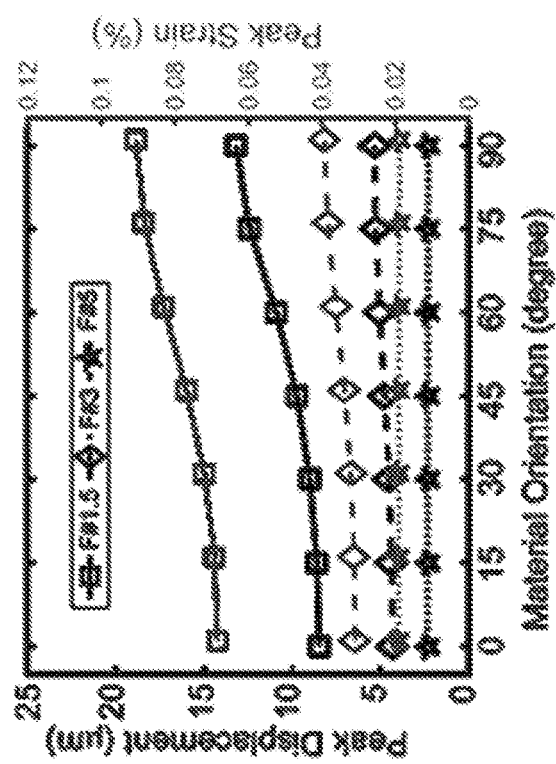
Figure 11B:
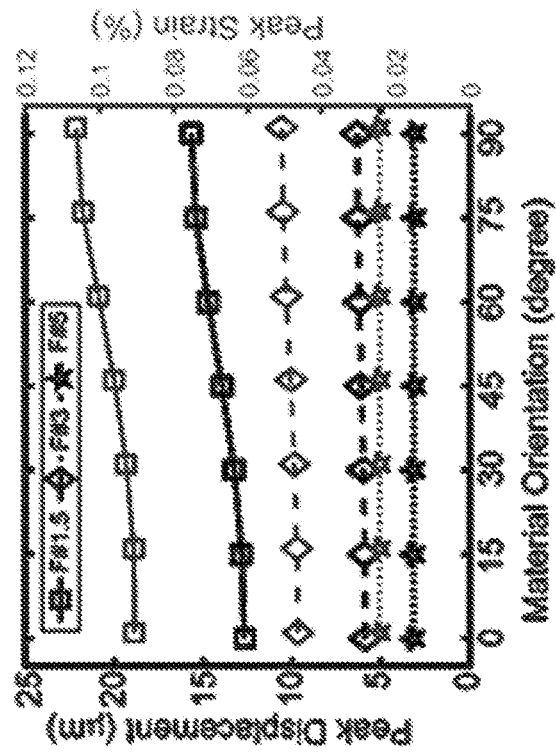
Figure 11C:
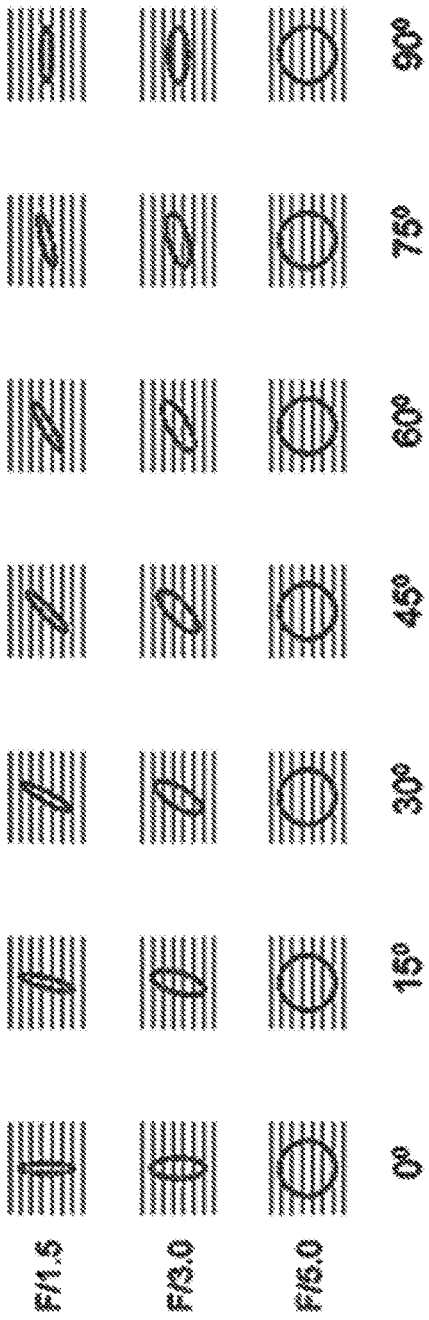

FIGS. 11A through 11C show peak displacement (PD, left y-axis) and peak strains (PS, right y-axis) versus PSF-material orientation for ARFI focal configurations of F/1.5, 3, and 5, respectively.

Figure 12A:
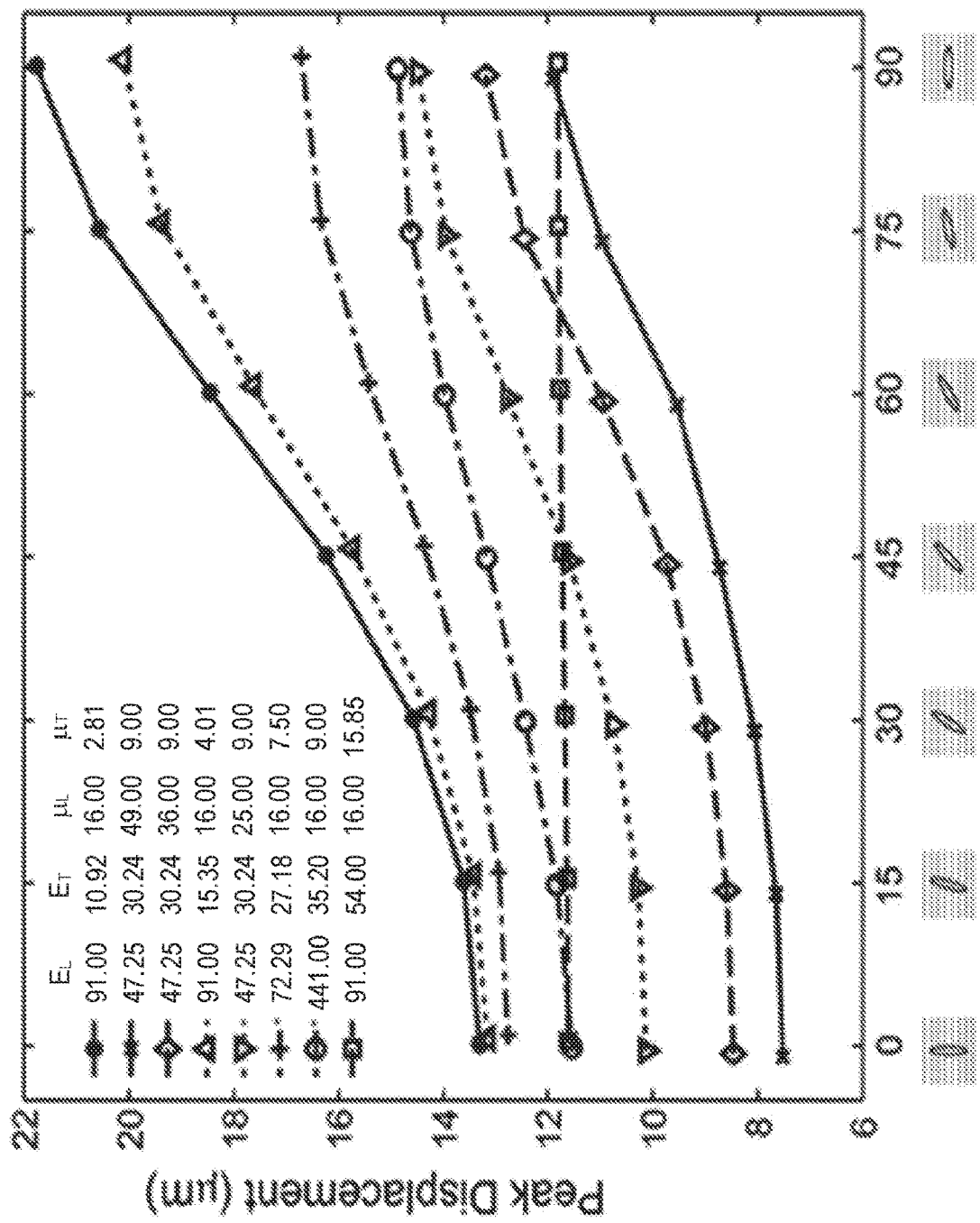

FIG. 12A shows PD as a function of PSF-material orientation for the F/1.5 2D ARFI PSF focal configuration in eight TI materials.

Figure 12B:
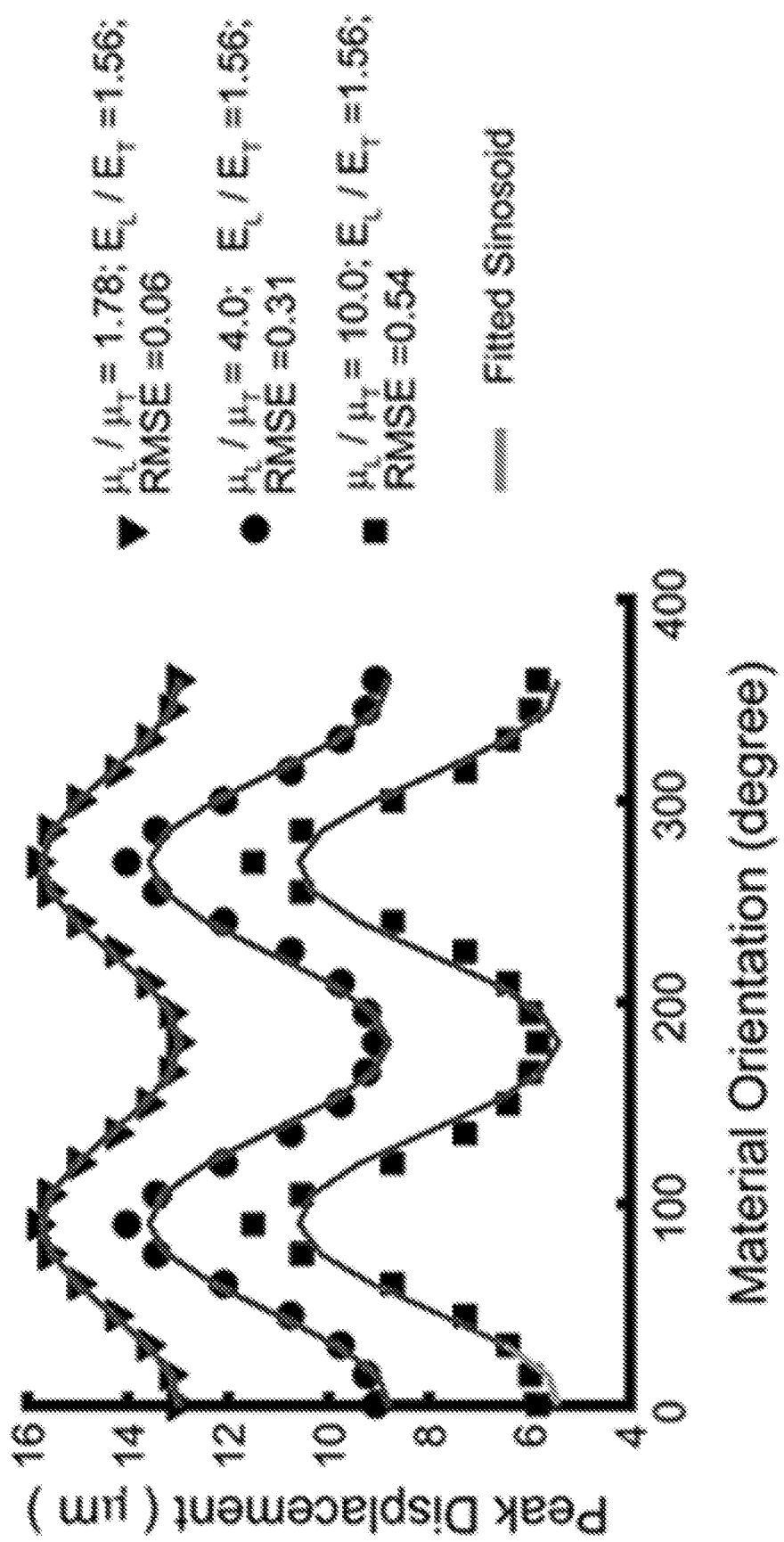

FIG. 12B shows PD as a function of material-PSF orientation for angles up to 360° for the F/1.5 2D ARFI PSF focal configuration in three TI materials with fitted sinusoidal function and root mean square error of the fit.

FIGS. 13A through 13D show ratios of PDs ($PD_{90}/PD_0$) versus degree of material anisotropy (ratio of Young's moduli or ratio of shear moduli) for F/1.5, 3, 4, and 5, respectively, 2D ARFI PSF focal configurations.

Figure 14B:
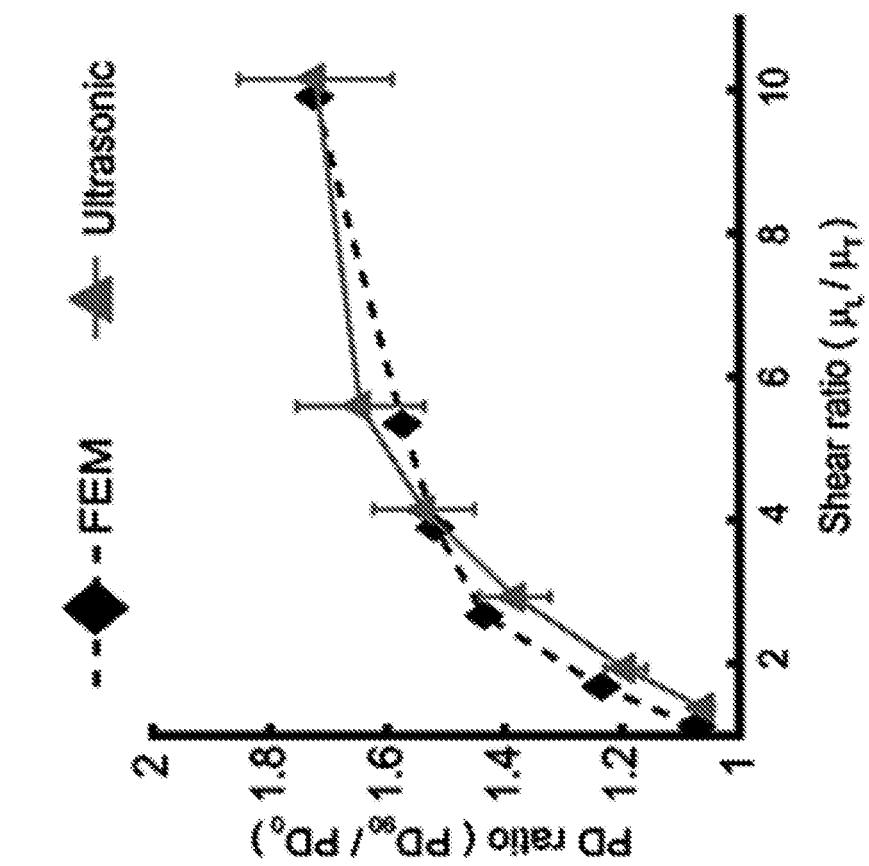
Figure 14A:
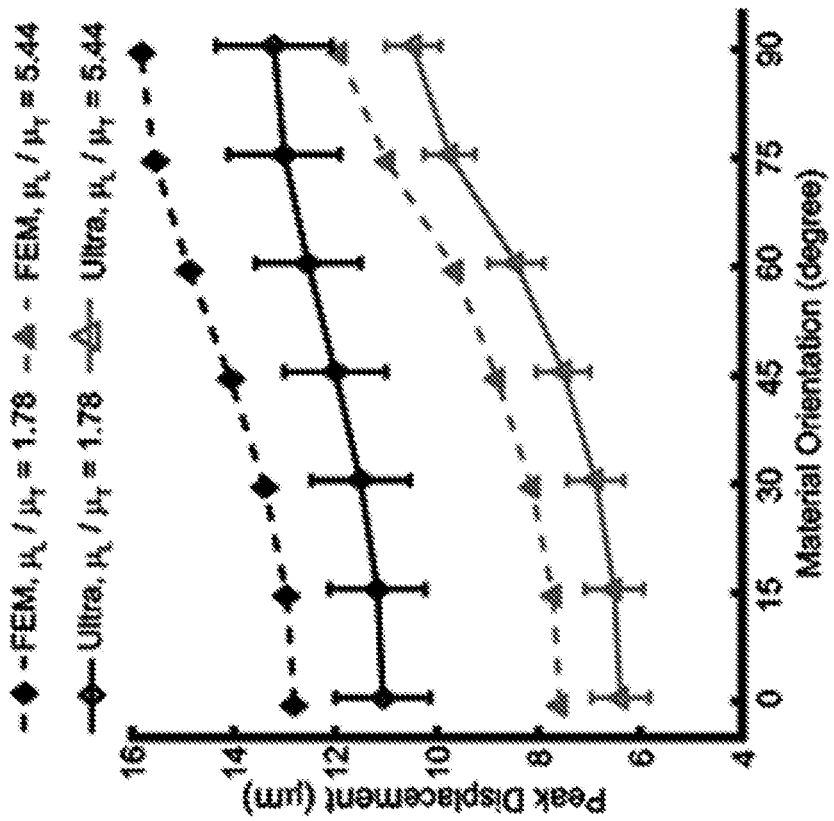

FIG. 14A shows finite element method (FEM)-derived and ultrasonically-tracked PD in two representative TI materials.

FIG. 14B shows FEM-derived and ultrasonically-tracked ratio of PDs ($PD_{90}/PD_0$) versus the ratio of shear moduli ($\mu_L/\mu_T$) for F/1.5 2D ARFI PSF focal configuration.

Figure 15B:
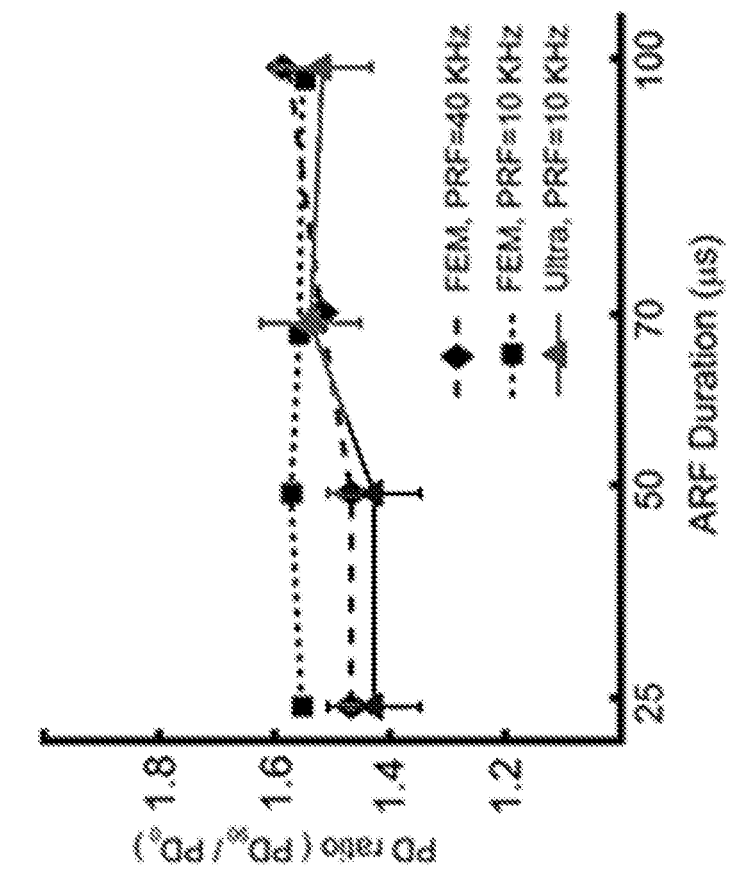
Figure 15A:
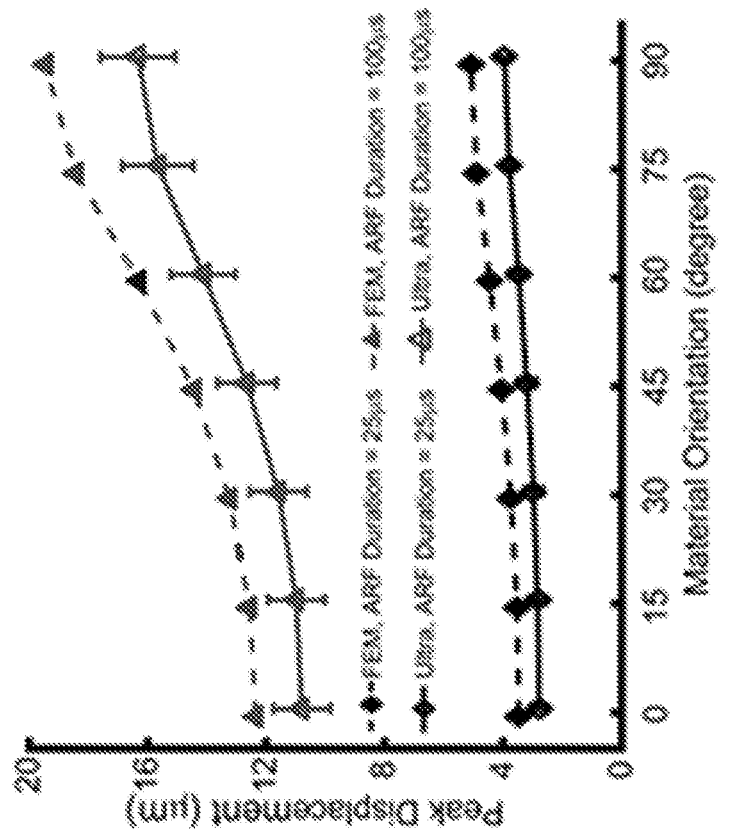

FIG. 15A shows FEM-derived and ultrasonically-tracked PD in a representative TI material ($E_L$=27.36 kPa, $E_T$=27.09 kPa, $\mu_L$=36 kPa, and $\mu_T$=9 kPa) as a function of PSF-material orientation for the F/1.5 2D ARFI PSF focal configuration.

FIG. 15B shows FEM-derived (dashed lines) and ultrasonically-tracked (solid lines) ratio of PDs ($PD_{90}/PD_0$) in the representative material versus ARF duration for F/1.5 2D ARFI PSF focal configuration.

Figure 16:
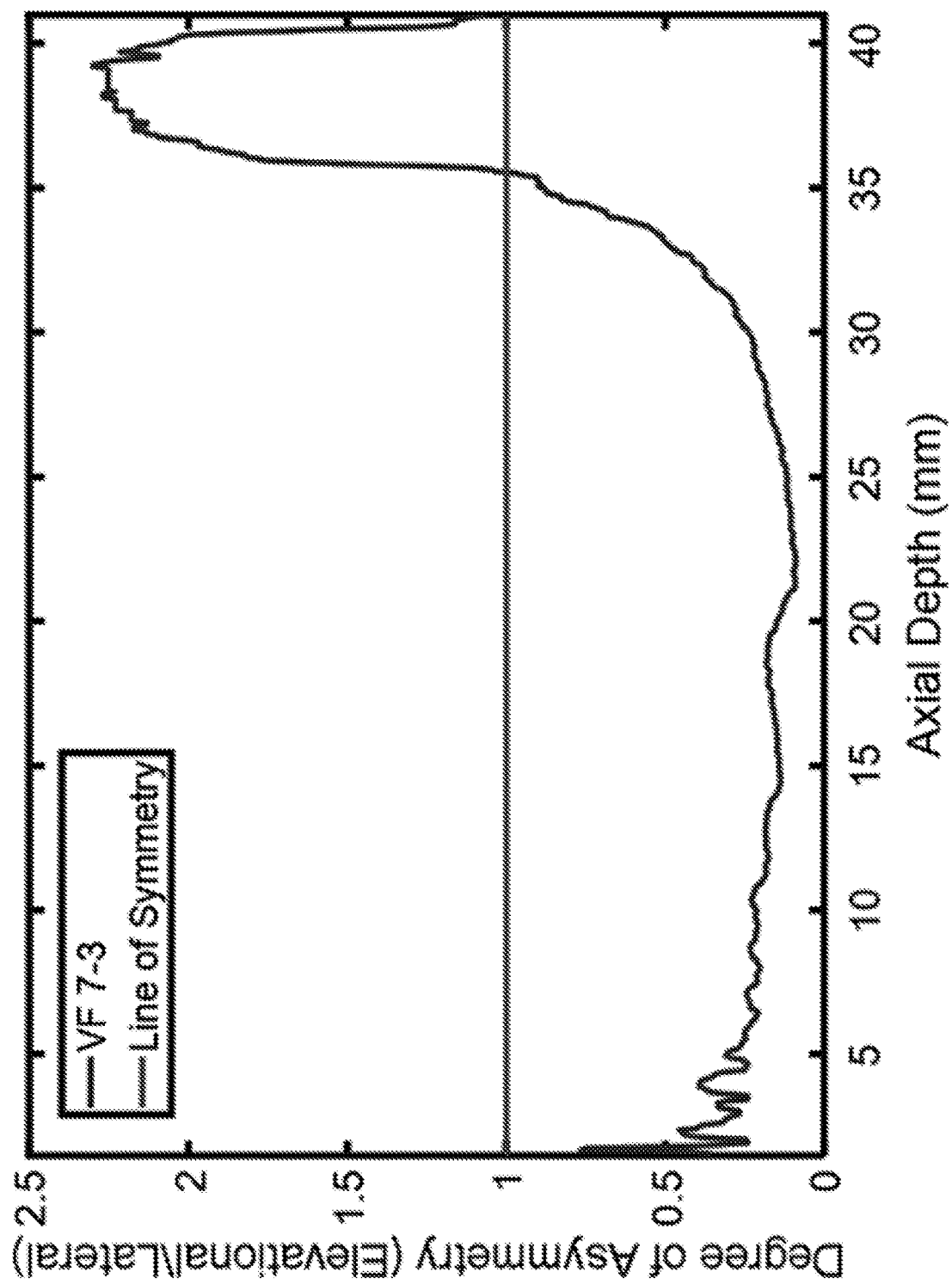

FIG. 16 is a graph of the degree of asymmetry of an ARF excitation as a function of depth.

Figure 17:
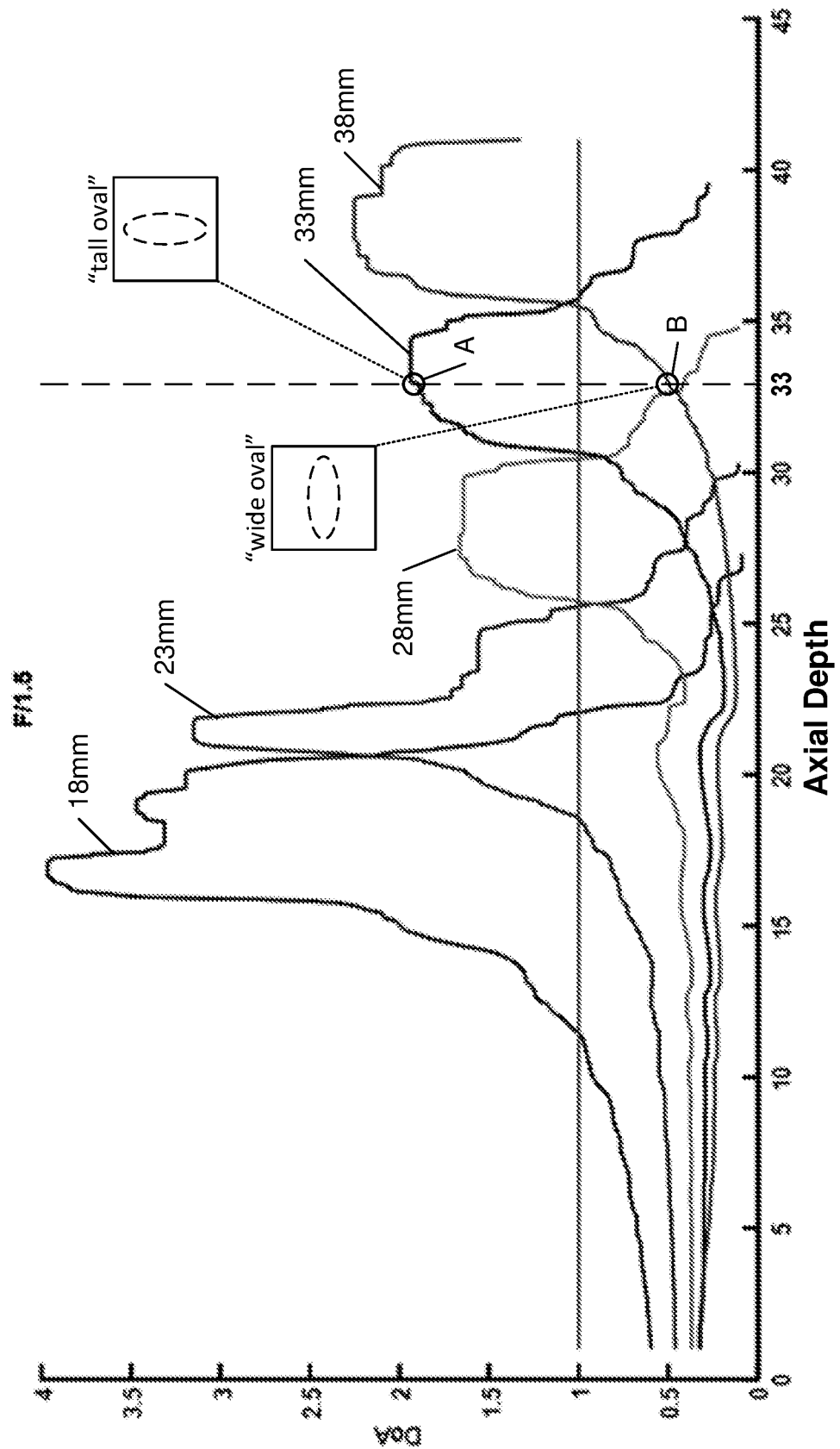

FIG. 17 is a graph of the degree of asymmetry of an ARF excitation as a function of depth for five different excitations, each having a different focal depth.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Figure 1A:
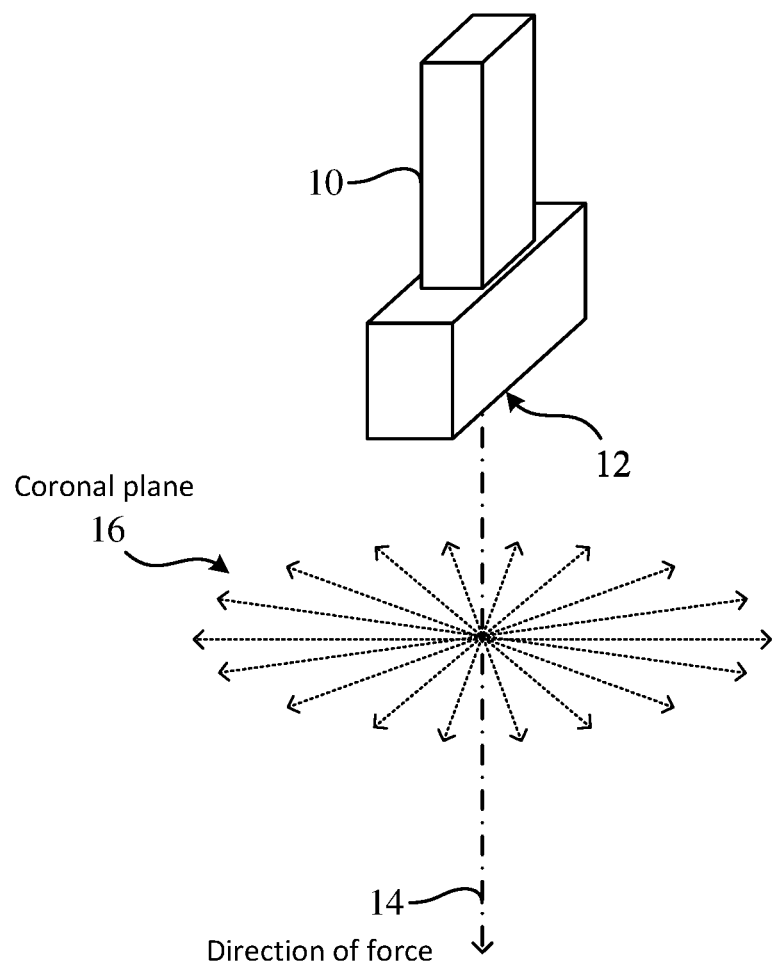
FIG. 1A illustrates an ultrasound transducer according to an embodiment of the subject matter described herein.

FIG. 1A illustrates an ultrasound transducer according to an embodiment of the subject matter described herein. In the embodiment illustrated in FIG. 1A, a transducer 10 includes an ultrasonic emitter array 12, which produces an acoustic radiation force (ARF) having a direction of force 14. A coronal plane 16 is defined as the plane normal to the direction of force 14. In the embodiment illustrated in FIG. 1A, the ultrasonic emitter array 12 comprises a linear array of emitter elements, and thus may alternatively be referred to as "linear array 12".

Figure 1B:
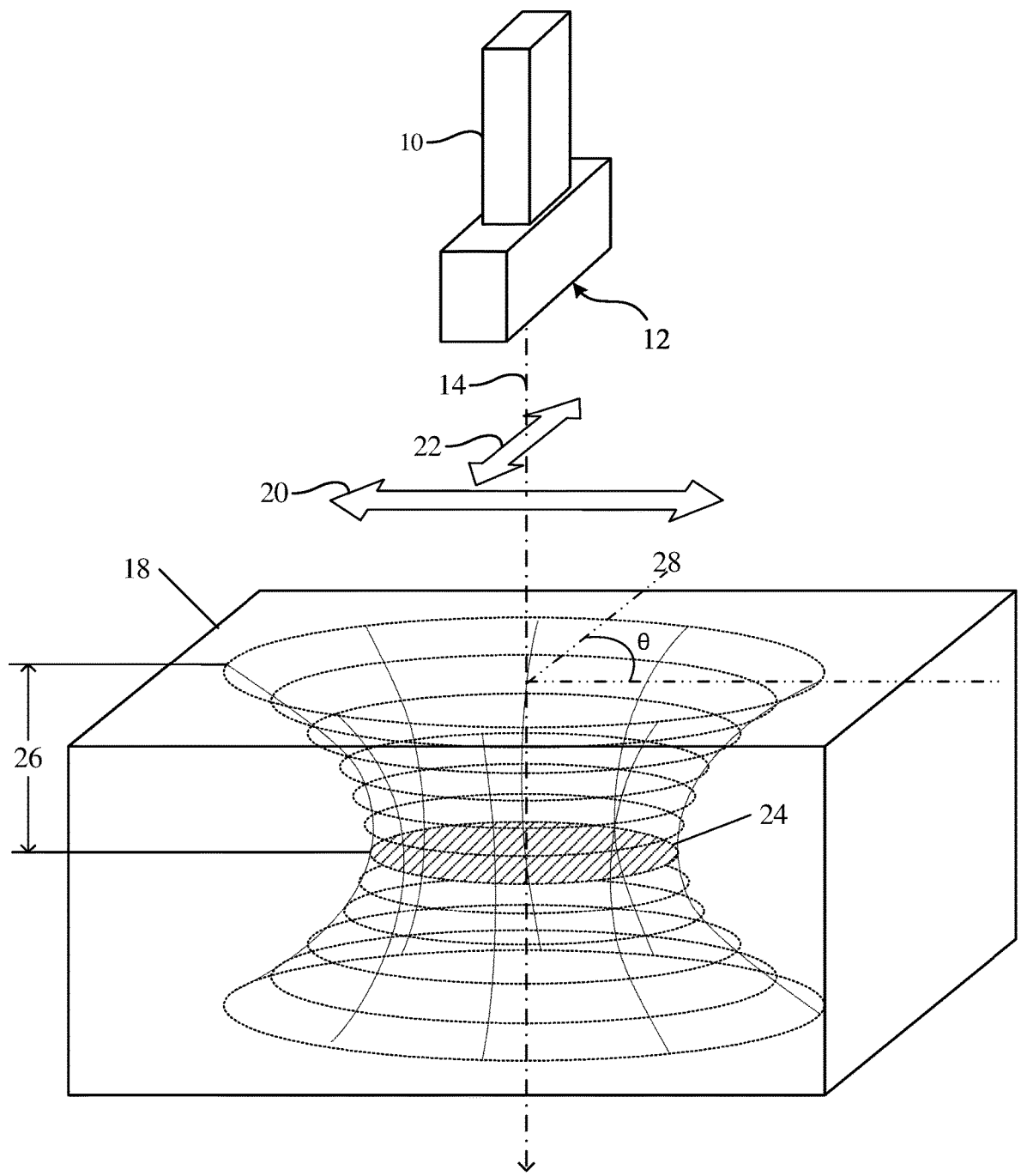
FIG. 1B illustrates the ultrasound transducer in use over a material sample, showing an oval force profile produced within the material sample.

FIG. 1B illustrates the ultrasound transducer in use over a material sample, showing an oval force profile produced within the material sample. In the embodiment illustrated in FIG. 1B, the transducer 10 produces a force having a direction 14. The force is directed into a material sample 18, which may be tissue. In one mode of operation, the transducer 10 produces a force having an oval-shaped profile. In another mode of operation, the transducer produces a force having a circular or other profile with equi-length axes.

In the embodiment illustrated in FIG. 1B, the transducer 10 is producing a force having an oval or other profile with a long axis 20 and a short axis 22. The shape delineated using dotted lines within the material sample 18 is intended to illustrate the point that the acoustic force produced by the transducer 10 has a point of highest energy 24—represented by a shaded oval—located at a focal depth 26 within the material 18. Above and below the focal depth 26, the size of the focal area expands and thus has a smaller energy per volume.

In the example illustrated in FIG. 1B, the shape of the force profile at focal depth is an oval. The long axis of the oval force profile 24 has an angle theta (Θ) relative to an arbitrarily chosen reference vector 28 associated with the material sample 18. For a transducer with a linear array of elements, the long axis of force 20 is perpendicular to the long axis of the array. To change the angle theta (Θ), it is necessary to physically rotate the linear array 12 around an axis of rotation aligned with the direction of force 14. In another mode of operation (not shown in FIG. 1B) the shape of the force profile at focal depth is circular.

Figure 2:
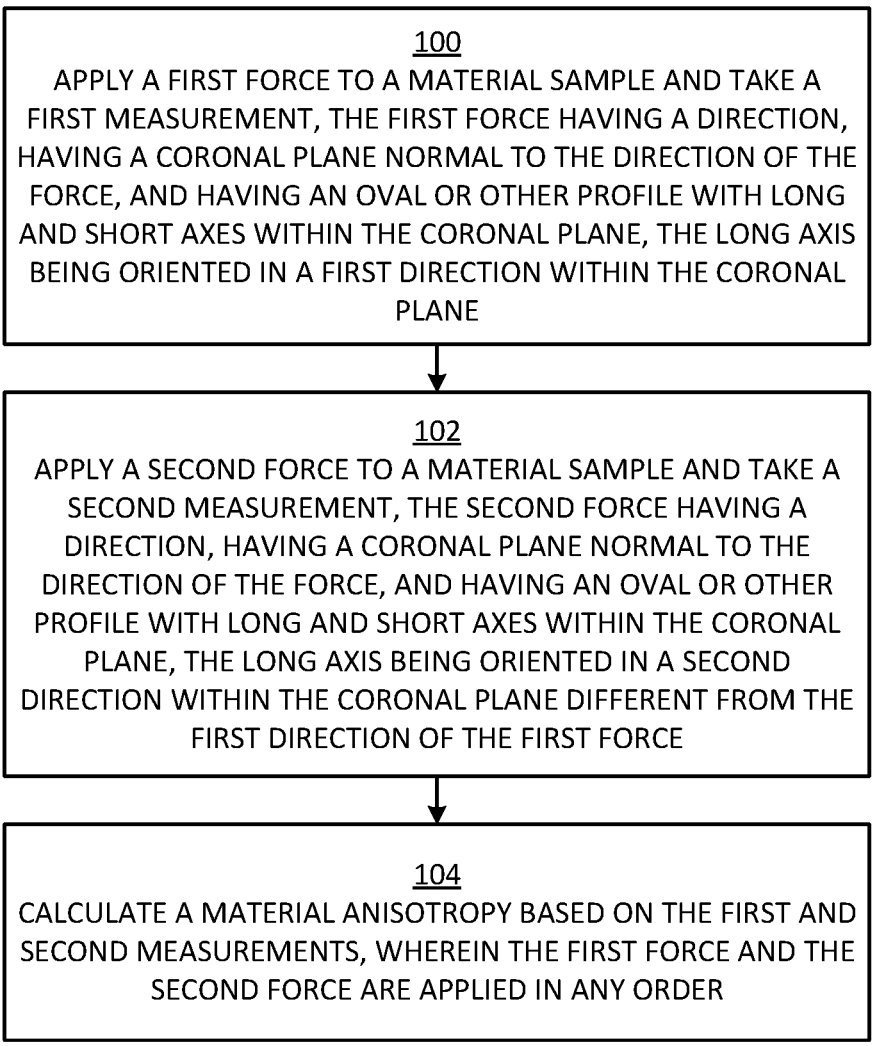
FIG. 2 illustrates a flow chart for an exemplary process for assessing material anisotropy according to an embodiment of the subject matter described herein.

FIG. 2 illustrates a flow chart for an exemplary process for assessing material anisotropy according to an embodiment of the subject matter described herein. In the embodiment illustrated in FIG. 2, the method includes:

applying a first force to a material sample and taking a first measurement, the first force having a direction, having a coronal plane normal to the direction of the force, and having an oval or other profile with long and short axes within the coronal plane, the long axis being oriented in a first direction within the coronal plane (step 100);

applying a second force to the material sample and taking a second measurement, the second force having a direction, having a coronal plane normal to the direction of the force, and having an oval or other profile with long and short axes within the coronal plane, the long axis being oriented in a second direction within the coronal plane different from the first direction of the first force (step 102); and calculating a material anisotropy based on the first and second measurements (step 104), wherein the first force and the second force are applied in any order.

It is noted that the first and second forces may, but need not always, occupy the same coronal plane. For example, a first oval force may have one orientation within a coronal plane and a second oval force may have a different orientation within the same coronal plane, e.g., at the same axial depth. In another example, a first oval force may occupy one coronal plane at a first axial depth and a second oval force may occupy another coronal plane at a second axial depth different from the first axial depth. Other combinations of orientation, axial depth, focal points, or other characteristics, are within the subject matter of the present disclosure.

It is also noted that the forces may be applied at a wide range of depths along the axis of force. For example, one pair of forces having different profiles or orientations may be applied at one depth, another pair of forces may be applied at a different depth, and so on. Likewise a pair of forces may be applied at one set of respective depths, another pair of forces may be applied at another set of respective depths, and so on.

It is also noted that while most of the examples presented herein describe operations that involve a pair of forces, the concepts and techniques described herein may also be implemented using more than two forces and/or using more than two force profiles or orientations.

In one embodiment, multiple measurements may be made at a variety of different angles. For example, rather than looking at the ratio of values measured at 0 and 90 degrees to reflect anisotropy, the method may include looking at the values achieved at 0, 10, 20, 30, 40, . . . 90 and larger degree angles and evaluate the measured value versus orientation angle. In alternative embodiments, more than two orientation angles could be measured and the method may include evaluation of more than just the ratio of values measured at these orientations.

FIGS. 3, 4, and 5 illustrate flow charts showing portions of an exemplary process for taking a material measurement according to an embodiment of the subject matter described herein. In the embodiment illustrated in FIG. 3, the method includes:

applying a first force to a material sample and taking a first measurement, the first force having a direction, having a coronal plane normal to the direction of the force, and having an oval or other profile with long and short axes within the coronal plane, the long axis being oriented in a first direction within the coronal plane (step 200);

applying a second force to the material sample and taking a second measurement, the second force having a direction, having a coronal plane normal to the direction of the force, and having a circular or other profile with equi-length axes within the coronal plane (step 202); and normalizing the first measurement using the second measurement to produce a first normalized measurement, wherein the first force and the second force are applied in any order (step 204).

In the embodiment illustrated in FIG. 4, the process described in FIG. 3 continues with the following:

applying a third force to a material sample and taking a third measurement, the third force having a direction, having a coronal plane normal to the direction of the force, and having an oval or other profile with long and short axes within the coronal plane, the long axis being oriented in a second direction within the coronal plane different from the first direction of the first force (step 300); and normalizing the third measurement using the second measurement to produce a second normalized measurement (step 302), wherein the first force, the second force, and the third force are applied in any order.

In the embodiment illustrated in FIG. 5, the process described in FIG. 3 continues with the following alternative steps to FIG. 4:

applying a third force to a material sample and taking a third measurement, the third force having a direction, having a coronal plane normal to the direction of the force, and having an oval or other profile with long and short axes within the coronal plane, the long axis being oriented in a second direction within the coronal plane different from the first direction of the first force (step 400);

applying a fourth force to the material sample and taking a fourth measurement, the fourth force having a direction, having a coronal plane normal to the direction of the force, and having a circular or other profile with equi-length axes within the coronal plane (step 402); and normalizing the third measurement using the fourth measurement to produce a second normalized measurement (step 404), wherein the first force, the second force, the third force, and the fourth force are applied in any order.

FIG. 6 illustrates a flow chart for an exemplary process for taking a material measurement according to an embodiment of the subject matter described herein. In the embodiment illustrated in FIG. 6, the method includes:

applying a first force to a material sample and taking a first measurement, the first force having a direction, having a coronal plane normal to the direction of the force, and having a circular or other profile with equi-length axes within the coronal plane (step 500);

applying a second force to the material sample and taking a second measurement, the second force having a direction, having a coronal plane normal to the direction of the force, and having a circular or other profile with equi-length axes within the coronal plane (step 502); and determining a material property based on a difference between the first measurement and the second measurement (step 504), wherein the first force and the second force are applied in any order.

FIG. 7 is block diagram illustrating a system for taking a material measurement, which may include determining material anisotropy, according to an embodiment of the subject matter described herein. In the embodiment illustrated in FIG. 7, the system includes a subsystem for force generation 30, a subsystem for motion dynamics observation 32, a subsystem for displacement calculation 34, a subsystem for parameterization 36, a subsystem for mathematical calculation 38, and a subsystem for producing system output 40.

The force generation subsystem 30 may produce ARF, a magnetic field, and/or a mechanical indentation. In the embodiment illustrated in FIG. 2, the force generation subsystem 30 produces two forces directed towards a material sample, one force having a first orientation (orientation 1) in the coronal plane and the other force having a second orientation (orientation 2) in the coronal plane.

The motion dynamics observation subsystem 32 may make measurements based on ultrasound, magnetic resonance imagery, optical input (such as but not limited to pictures, videos, etc., including from high-speed cameras), optical coherence tomography, or using a mechanical means, such as but not limited to a micrometer. It should be noted that the angles of the forces and measurements with respect to the sample as shown in FIG. 7 were chosen for illustration purposes only and are not intended to convey any particular orientation.

The displacement calculation subsystem 34 receives data produced by the motion dynamics observation subsystem 32 and calculates displacement of the sample. In the embodiment illustrated in FIG. 7, the displacement calculation subsystem 34 receives data for each measurement.

The parameterization subsystem 36 uses displacement information received from the displacement calculation subsystem 34 to determine certain parameters or material properties/material characteristics, such as PD, a value for TAU, time to peak (TTP), recovery time, Viscoelastic Response (VisR) relative elasticity, VisR relative velocity, etc.

The mathematical calculation subsystem 38 uses the parameters produced by the parameterization subsystem 36 to produce an output value, which is sent to system output subsystem 40. The calculations that may be performed by the mathematical calculation subsystem 38 include, but are not limited to, normalization of one data using another data; calculation of ratios of the two output values; and coefficient adjustment.

It will be understood that applying a force having a particular orientation or force profile may involve applying the force once or may involve applying the force a plurality of times. Applying a force a plurality of times may involve applying a force for a first duration of time, ceasing to apply the force for a second duration of time (e.g., pausing), and repeating the apply/pause cycle multiple times. The duration of time during which the force is applied, and/or the duration of the pause between one application of the force and a subsequent application of the force, does not need to be constant during the course of the repetitions. Likewise, the force that is applied need not be unchanged over the course of the repetitions.

In one embodiment, a plurality of applications of force and/or measurements is performed at different angles from each other. The angle difference between any two applications of force/measurements does not need to be 90 degrees. For example, a first application of force and measurement may be taken in one orientation and a second application of force and measurement may be taken at another orientation, where the difference in orientation may be 75 degrees, 50 degrees, or any other difference in orientation.

Methods

Finite element simulations of a 1.25 mm radius, TI elastic, cylindrical inclusion embedded in an isotropic elastic material were performed using a commercially available Finite Element Method (FEM) solver, "LS-DYNA". A simulated 2D, 38 mm square matrix array transducer with 1922 elements, simulated with Field II, was used to model the ARF excitation geometry. Each phantom was excited (for 70 us @ 4.21 MHz) by an asymmetrical ARF point spread function, with the long axis of the excitation oriented first along and then across the TI material's axis of symmetry.

The aperture was then swept laterally in 0.35 mm increments to acquire data along a 2D field of view. The degree of anisotropy was then computed as the ratio of the resultant peak displacements, and parametric images of degree of anisotropy and peak ARFI-induced displacement were rendered.

The imaging simulations were repeated for a total of 12 materials with differing material properties. The shear modulus of the isotropic material was held static at 1.7 kPa, while the longitudinal and transverse shear moduli of the TI material were varied from 5 to 10 and 5 to 30 kPa, in steps of 5 kPa, respectively. Contrast ratios were computed for each inclusion in the resulting parametric anisotropy images. Contrast-to-noise ratios (CNR) were also computed for the anisotropy and peak displacement parametric images.

The axial range over which anisotropy measurements could be performed was also investigated using the same 12 material combinations, in a homogeneous TI material model. The axial range was determined by measuring the depth over which the ratio of peak displacements in the homogenous TI material varied less than 5% for all 12 materials. The range was reported as mean±standard deviation.

Using the same methods, a three-dimensional (3D) image of anisotropy was also simulated in a single material model with background shear modulus 1.7 kPa and inclusion shear moduli of 5 and 30 kPa in the transverse and longitudinal directions, respectively. The 3D image was formed by sweeping the aperture in both the lateral and elevational directions and taking the ratio of the peak displacements at each position.

Results

For each of the six phantoms with ratios of longitudinal to transverse shear moduli ranging from 1.0 to 6.0 in steps of 1.0, the ratios of peak displacements increased proportionally with an increase in the ratio of shear moduli (1.00±0.08; 1.06±0.08; 1.10±0.07; 1.13±0.07; 1.15±0.07; 1.17±0.07). CNR measurements for peak displacement with the long axis of the force aligned with the axis of symmetry ranged from −25.7 dB to −16.9 dB from the least to most anisotropic lesion. With the long axis of the force normal to the axis of symmetry, the CNR ranged from −4.3 dB to +3.4 dB, from the least to most anisotropic lesion. Anisotropy images, created from the ratio of peak displacements yielded CNR values ranging from +18.7 dB to +20.9 dB in the same lesions. The axial extent of the anisotropy measurement field set was found to be 12.47±2.35 mm for the materials used in this work. Using the 3D imaging technique, the degree of anisotropy measured throughout the 3D lesion was 1.12±0.04.

Conclusions

The results of the phantom simulations indicate that the measured degree of anisotropy is directly proportional to the modeled ratio of shear moduli. This work has also shown that the degree of anisotropy measurement is valid over an axial range larger than the simulated inclusion, confirming the validity of phantom simulations. These data indicate that degree of anisotropy can be imaged using a ratio of peak displacements induced by a 2D matrix transducer.

To date, no other known ultrasound-based system is able to make images of anisotropy directly from the ratio of peak displacements. Other technologies that are able to make such images are dependent on the propagation of shear waves, which leads to decreased spatial and temporal resolution. Our method of creating anisotropy images depends only on the maximal displacement at each position through depth, which makes the resolution of our technique finer than that of shear-wave based methods. Our technique uses a two-dimensional matrix array transducer to create the appropriate forcing geometries in each orthogonal direction. Currently, two-dimensional matrix array transducers are expensive to build and have been demonstrated for producing radiation force in limited cases. It is noted that a 2D matrix is not necessarily needed to eliminate rotation. A row-column or other configuration of transducer could be used. In addition, as discussed below, it is possible to eliminate rotation by adjusting the focal depth.

In Silico Verification

Many soft tissues exhibit anisotropic mechanical properties. The simplest anisotropic material model is that of a TI material, which is defined by a plane of isotropy perpendicular to an AoS. The TI material model has been used to represent the strong anisotropy in mechanical properties observed in muscles, tendons, kidney, brain white matter, bones, and breast.

The mechanical properties of TI materials may be described in terms of Young's and shear moduli; however, the relationship between these moduli is more complex in TI than in isotropic materials. In linear, elastic, isotropic, incompressible (Poison's ratio v≅0.5) materials, the Young's modulus (E) is related to the shear modulus ($\mu$) according to E≅3$\mu$. The shear modulus may be estimated from the shear wave velocity (V) as, $\mu = \rho V^2$, where $\rho$ is the density of the material.

In contrast, for a TI material, the Young's and the shear moduli differ along versus across the AoS. In the limit of small displacements, the constitutive equation for a linear elastic solid is defined by Hooke's law as $$\sigma_{ij} = c_{ijkl} \varepsilon_{kl} \tag{1}$$

where, $\sigma_{ij}$ is a stress tensor, $\varepsilon_{kl}$ is an infinitesimal strain tensor, and $c_{ijkl}$ is a fourth-order stiffness tensor representing the properties of a material. Due to symmetry in TI materials, $c_{ijkl}$ contains five independent elastic constants (instead of 81). The reduced $c_{ijkl}$ with five independent elastic constants will be denoted as c. The compliance matrix $s = c^{-1}$ can be expressed as follows $$s = c^{-1} = \begin{pmatrix} \frac{1}{E_L} & -\frac{v_{LT}}{E_L} & -\frac{v_{LT}}{E_L} & 0 & 0 & 0 \\ -\frac{v_{LT}}{E_L} & \frac{1}{E_T} & -\frac{v_{TT}}{E_T} & 0 & 0 & 0 \\ -\frac{v_{LT}}{E_L} & -\frac{v_{TT}}{E_T} & \frac{1}{E_T} & 0 & 0 & 0 \\ 0 & 0 & 0 & \frac{1}{\mu_T} & 0 & 0 \\ 0 & 0 & 0 & 0 & \frac{1}{\mu_L} & 0 \\ 0 & 0 & 0 & 0 & 0 & \frac{1}{\mu_L} \end{pmatrix} \tag{2}$$

where $$\mu_T = \frac{E_T}{2(1 + v_{TT})} \tag{3}$$

$E_L$ and $E_T$ are the longitudinal and the transverse Young's moduli, $\mu_L$ and $\mu_T$ are the longitudinal and transverse shear moduli, and $v_{TT}$ and $v_{LT}$ are Poisson's ratio in the plane of isotropy and in the plane of symmetry, respectively. Longitudinal (L) and transverse (T) directions are defined relative to the AoS. The fractional volume change of an infinitesimal volume subjected to stress (i.e., dilatation) must be zero for an incompressible material. So, Poisson's ratio for an incompressible TI material is given as.

$$v_{TT} = 1 - \frac{E_T}{2E_L} \tag{4}$$

$$v_{LT} = \frac{1}{2}$$

Note that, incompressible TI materials are defined by three material constants: $\mu_T$, $\mu_L$, and $$\frac{E_T}{E_L}.$$

An elliptical propagation of shear waves can be induced by ARFI excitation in incompressible TI materials. More specifically, the components of the shear wave group velocities form an ellipse, and they can be found from the following relationship in the Cartesian coordinate system $$\frac{(V_x \cos\theta + V_y \sin\theta)^2}{V_L^2} + \frac{(V_x \sin\theta - V_y \cos\theta)^2}{V_T^2} = 1 \tag{5}$$

where, $(V_x, V_y)$ defines the path of a point on the ellipse, $V_L$ and $V_T$ are major and minor axis of the ellipse, and $\theta$ is the angle between the major axis and the X-axis. $\theta$, $$V_L = \sqrt{\frac{\mu_L}{\rho}}, \text{ and } V_T = \sqrt{\frac{\mu_T}{\rho}}$$

also define the angle between the AoS and X-axis, SWV along the AoS, and SWV across the AoS, respectively. The orientation of the ellipse gives the orientation of the material's AoS.

FIG. 8A shows the group velocity [ms$^{-1}$] of a shear wave travelling in a TI material with $E_T$=34.56 kPa, $E_L$=216 kPa, $\mu_T$=9 kPa, $\mu_L$=25 kPa and $\rho$=1 gcm$^{-3}$. The major axis length, minor axis length, and orientation of the ellipse give the SWV along the AoS (5 ms$^{-1}$), across the AoS (3 ms$^{-1}$), and orientation of the material's AoS (60°), respectively.

The anisotropy of TI materials has been assessed as the ratio of SWV measured along versus across the AoS, or the "fractional anisotropy". However, SWV measurement is subject to error from tissue inhomogeneities within the measurement region, and the requirement for observations of displacement over time at multiple lateral locations reduces frame rate unless a plane wave imaging method is implemented. The drawback of plane wave imaging is a lack of transmit-focusing, which leads to loss of SNR and resolution and challenges applications in deep tissues and obese patients. To increase the SNR, coherent spatial compounding may be employed. However, coherent compounding reduces the frame rate relative to conventional plane wave imaging. Assessing the degree of anisotropy in a TI material in a single, focal spatial location could help to reduce error from inhomogeneities and increase frame rates without sacrificing lateral resolution or SNR.

The subject matter disclosed herein includes ARFI imaging, in which induced displacements are observed in only the ARFI region of excitation (ROE), as a novel approach to describing the degree of anisotropy in TI materials. The rationale for this approach is that the mechanical response of TI materials depends on the direction of loading with respect to the AoS. For example, it has been shown that displacements were higher when the long axis of an asymmetrical indenter was aligned parallel versus perpendicular to the direction of the AoS in TI elastic materials. The inventors have determined that ARFI-induced PDs will be larger when the long axis of an asymmetrical ARFI2D PSF is aligned along versus across the AoS. The inventors have determined that the ratio of PDs achieved with the long axis of an asymmetrical ARFI-2D PSF aligned along versus across the AoS reflects the degree of anisotropy in TI materials.

The concept was first proven in silico, including an expanded description of the employed in silico model, validation of the TI nature of the modeled materials, new results and analyses for 52 different simulated TI materials, implementation of simulated ultrasonic displacement tracking, variation in the ARF duration, and a comprehensive discussion of the significance of the reported results. Table 1, below, lists the used symbols.

TABLE 1

| | |
|---|---|
| $E_L$ | Longitudinal Young's modulus |
| $E_T$ | Transverse Young's modulus |
| $\mu_L$ | Longitudinal shear modulus |
| $\mu_T$ | Transverse shear modulus |
| $\dfrac{\mu_L}{\mu_T}$ | Ratio of the Longitudinal and Transverse shear moduli |
| $\dfrac{E_L}{E_T}$ | Ratio of the Longitudinal and Transverse Young's moduli |
| $PD_{angle}$ | Peak displacement when the AoS is oriented at angle (0°, 15°, 30°, 45°, 60°, 75°, and 90°) |
| $\dfrac{PD_{90}}{PD_0}$ | Ratio of peak displacement (PD) when the AoS is oriented along versus across the long axis of the ARFI-2D PSF |

Methods

FIG. 8B shows the XYZ coordinate system used to describe the material's AoS orientation with respect to the ARFI excitation 2D PSF, where lateral axis=Y axis, elevational axis=X axis, and axial axis=Z-axis. The TI material's AoS is oriented along the X-axis, with the plane of isotropy in the YZ-plane and the plane of symmetry in the XZ-plane. Mechanical properties are similar in the plane of isotropy. An asymmetrical ARFI 2D PSF in the lateral-elevational plane, produced at the focal depth by a linear array transducer, is represented by a gray ellipse. For this material-PSF arrangement, the long axis of the PSF is aligned with the AoS, for a "90°" orientation A FEM model was used to simulate the dynamic responses of an elastic TI solid to an ARFI excitation. The 3D, dynamic response of the elastic TI solid was solved through the balance of linear momentum using the software application "LS-DYNA3D" (Livermore Software Technology corp. Livermore, Calif.) with an explicit time-domain method. The axial, lateral, and elevational extents of the Finite Element (FE) mesh were each 25 mm for the purpose of measuring SWV to validate the material model; however, these values were adjusted to 25 mm, 12 mm, and 12 mm, respectively, for greater computational efficiency while estimating anisotropy based on the ARFI PD at the focal depth. The axial, lateral, and elevational dimensions spanned 25 mm to 50 mm, −6 mm to 6 mm, and −6 mm to 6 mm, respectively. The FE mesh element size was 0.2×0.2×0.2 $mm^3$.

The center of the transducer was aligned to the origin of the XYZ coordinate system. A built-in material model (MAT_ORTHOTROPICTROPIC_ELASTIC in LS-DYNA3D) was used to simulate 52 different homogeneous, linear, elastic TI materials with the following ranges of elastic constants: $E_T$=6.53-89.69 kPa; $E_L$=15.4-486.34 kPa; $\mu_T$=1.67-29.7 kPa; $\mu_L$=10-90 kPa. In the TI elastic material, compressibility is controlled by the value of one Poisson's ratio, $v_{LT}$ that must equal 0.5 to retain perfect incompressibility according to equation (4). However, a perfectly incompressible material cannot be modeled in DYNA. To overcome this limitation, we set the simulated value of $v_{LT}$ to 0.499, which approaches incompressibility conditions. Then, the second Poisson's ratio ($v_{TT}$) for the simulated material was calculated using equation (4). Note that a Poisson's ratio of 0.499 has previously been implemented in DYNA simulations for isotropic materials and for TI materials. The density of all TI materials was fixed to $\rho$=1 $gcm^{-3}$.

Table 2 contains the elastic constants with ratio of shear and Young's moduli of all simulated materials. Note that these elastic constants were generally selected to reflect known muscle properties ($\mu_L$=16-55 kPa; $\mu_T$=1-9 kPa)). For example, values of the shear moduli were selected such that the SWV was faster along versus across the muscle fibers (i.e., the AoS), and Young's moduli were selected such that the materials were stiffer along than across the AoS. Further, to explore the utility of our technique in more extreme scenarios, we also created one highly and one minimally anisotropic TI material. A seven-element thick perfect matching layer (PML) was implemented around the mesh using the built-in material model (MAT_PML_ORTHO-TROPIC_ELASTIC in LS-DYNA3D) with matching to the elastic constants used in the MAT_ORTHOTROPIC-TROPIC_ELASTIC material model. The purpose of the PML layer was to simulate an infinite medium and remove spurious wave reflections from the boundaries of the mesh.

Using a linear acoustics modeling package, "Field II", the ARFI field was simulated by first computing the acoustic intensity at each nodal location based on the method described in. The Siemens VF7-3 linear array transducer parameters were used to calculate the acoustic intensity in Field II with a transmitting frequency of 4.21 MHz, a fixed elevational focus at 37.5 mm, and lateral focal configurations of F/1.5, 3, 4, and 5. The axial focal depth was fixed to 36 mm for all simulations. Field II-derived intensity values were scaled to a peak intensity of 10,000 $W/cm^2$, and the volumetric acoustic radiation force magnitude was calculated using the expression:

$$\vec{F} = \frac{2\alpha \vec{I}}{c} \tag{6}$$

where α is the absorption coefficient of the medium (assumed to be 0.5 dB/cm/MHz), $\vec{I}$ is the temporal-average beam intensity over a volume, and c is the speed of sound through the medium (assumed to be 1540 m/s).

The point load forces were calculated by spatially sampling the volumetric force. Point forces were then superimposed on the FE mesh, and the force magnitude was kept constant for 70 µs for all simulated materials. Additionally, for one representative material, the force magnitude was kept constant for 25 µs, 50 µs, 70 µs, and 100 µs. The simulation was allowed to run for 3.5 ms total, and data were sampled every 0.1 ms for all materials, approximating a conventional ARFI ensemble with 10 kHz pulse repetition frequency (PRF). Additionally, for one representative material, data were sampled every 25 µs, approximating a 40 kHz PRF.

The dimension of the generated displacements matrix with each simulation is four-dimensional (4D) (axial×lateral×elevational×time). PD over time at the center of the push was calculated. A 4D matrix of strain was calculated by taking the spatial gradient of displacements at each time instant. Similar to PD, PS was calculated over time at the center of the push. To study the effect of PSF-AoS orientation on PD and PS, the AoS of the TI materials was oriented at seven different angles: 0°, 15°, 30°, 45°, 60°, 75°, and 90°, where angle 0° and 90° correspond to the long axis of the ARFI-2D PSF being aligned across and along the material's AoS, respectively. Additionally, three representative materials were orientated from 0° to 360° at an interval of 15°.

To evaluate the impact of ultrasonic tracking on PDs in TI materials, simulation of ultrasonic tracking of ARF-induced displacement was performed. First, a three-dimensional Field II scatterer phantom with fully-developed speckle (31 scatterers per resolution cell) was defined to span the volume of the FEM mesh. Next, the FEM-derived displacements were used to linearly-interpolate scatterer positions for every time step in the ARFI ensemble using MATLAB (Mathworks Inc., Natick, Mass.). After generating the scatterer position matrices for each time step in the ARFI ensemble, the corresponding radio frequency (RF) lines were simulated using Field II. White Gaussian noise was added to each RF line using the awgn function in Matlab to simulate system signal to noise ratio (SNR) of 40 dB. The Siemens VF7-3 linear array transducer parameters were used to simulate tracking pulses with a transmitting frequency of 6.15 MHz and lateral focal configurations of F/0.75. Tracking pulses were focused at 36 mm axially on transmit, and dynamic focusing was used on receive. Motion tracking was performed using one-dimensional normalized cross correlation with a kernel length of 2λ. After motion tracking, PD was calculated. For each simulated TI material in a representative subset of six, ten unique phantoms with independent speckle realizations were generated.

To confirm that the modeled material was behaving as a TI material, ARFI-induced SWV along and across the AoS was measured for seven different material-PSF orientations, i.e. the long axis of the PSF was aligned at 0°, 15°, 30°, 45°, 60°, 75°, and 90° relative to the material's AoS. For each material-PSF orientation, the shear wave group velocities at angles from 0°-360° in the lateral-elevational plane were measured at the focal depth. Then, an ellipse was fit through the measured SWVs to determine the SWV along the AoS, the SWV across the AoS, and the orientation of the material's AoS. The velocities were related to TI material property according to equation (5).

D. Symmetry of ARFI Excitations

The spatial distribution of the ARFI 2D PSF was varied by changing the focal configuration, or F/#, defined as:

$$/\# = \frac{z}{D},$$

where z is the axial focal depth and D is the width of the active aperture. For a standard 1-D linear array, the lateral F/# is adjusted by electronically selecting the number of active elements, while the elevational $$F/\# = \frac{z}{h}$$

is set by me height (h) of the transducer elements and the fixed-focused lens. The lens of the Siemens VF7-3 linear array transducer has a fixed elevational focus at 37.5 mm. We used "xdc_focused_multirow" function in Field II to model the fixed elevational focus at 37.5 mm. To manipulate the degree of asymmetry of ARFI excitations at the desired focal depth, lateral focal configuration was adjusted, and degree of asymmetry was measured as the ratio of the lateral versus elevational extent of the ARFI 2D PSF. For example, for an F/1.5 lateral focal configuration at a focal depth of 36 mm, the lateral and elevational extents of the ARFI PSF were 1 mm and 3 mm, respectively, yielding a degree of asymmetry of 0.33. The degree of asymmetry of the ARFI-2D PSF at 36 mm for focal configurations of F/3, 4 and 5 was 0.69, 0.85, and 1.15, respectively.

FIGS. 9A through 9D show the spatial distribution of the ARFI-2D PSF in the lateral-elevational plane at the focal depth (36 mm) for focal configurations of F/1.5 (FIG. 9A), F/3 (FIG. 9B), F/4 (FIG. 9C), and F/5 (FIG. 9D) with their respective degree of asymmetry values. degree of asymmetry was measured as the ratio of the lateral versus elevational extent of the PSF. The intensity bar indicates normalized nodal force at the focal depth, with normalization relative to the maximum nodal force. The F/1.5 lateral focal configuration yielded the most asymmetric ARFI PSF, while a nearly symmetrical ARFI PSF was achieved for the F/5 lateral focal configuration.

Results

FIG. 10A shows elliptical shear wave propagation in a representative modeled TI material with $E_T$=34.56 kPa, $E_L$=216 kPa, $\mu_T$=9 kPa, $\mu_L$=25 kPa, and ρ=1 gcm$^{-3}$. The SWVs along and across the AoS are expected (from equation (5)) to be 5 ms$^{-1}$ and 3 ms$^{-1}$, respectively. The black dots represent the measured SWV at angles from 0°-360° and the fitted ellipse through these dots is shown as the black line.

FIG. 10B shows both expected (True) and measured (Measured) SWVs along and across the AoS for the seven material-PSF orientations. The true SWV was calculated from the analytical equation (equation (5)), whereas the measured SWV was calculated from the fitted ellipse. The maximum percentage of error in the measured SWV along and across the AoS was <2.5%.

FIG. 10C shows a plot of measured AoS orientations from the fitted ellipse versus true material AoS orientations, indicating the Pearson correlation coefficient was r=1.

FIGS. 11A through 11C show PD (left y-axis) and PS (right y-axis) versus PSF-material orientation for ARFI focal configurations of F/1.5, 3, and 5. FIGS. 11A and 11B show results for two different simulated TI materials, with the material in FIG. 11A having a higher degree of anisotropy. Metrics for material anisotropy were the ratio of the longitudinal and the transverse shear moduli ($\mu_L/\mu_T$) and the ratio of the longitudinal and transverse Young's moduli ($E_L/E_T$). The transverse and longitudinal Young's moduli and the transverse shear modulus were kept fixed for both materials ($E_T$=30.24 kPa, $E_L$=47.25 kPa, and $\mu_T$=9 kPa) but the longitudinal shear modulus was varied ($\mu_L$=36 kPa in FIG. 11A and $\mu_L$=16 kPa in FIG. 11B). Note that the PD and PS are higher in FIG. 11B than in FIG. 11A for the same focal configuration and orientation of the AoS because $\mu_L$ is lower in FIG. 11B than in FIG. 11A. For both materials, PD and PS spanned minimum to maximum values when the AoS was oriented from 0° to 90° for F/1.5 and F/3 ARFI focal configurations. However, PD and PS were constant across material orientations for the F/5 ARFI focal configuration.

FIG. 11C illustrates cross-sections of the 2D ARFI excitation PSFs in the lateral-elevational plane at the focal depth with respect to the alignment of the material's AoS. For asymmetrical ARFI excitations (F/1.3 and F/3), the long axes of the ARFI PSFs were observed to rotate with respect to the AoS for different orientations. However, the interrogating ARFI region was the same in all orientations for the symmetrical focal configuration (F/5).

Our data presentation from here forward will be limited to PD because PD and PS were observed to exhibit similar trends. To quantify the variability in PD with material-PSF orientation, we measured the ratio of PDs when the material's AoS was at 90° versus 0° (i.e., $PD_{90}/PD_0$). The ratio of PDs was 1.56 and 1.24 in the materials of panels (a) and (b), respectively when the ARFI focal configuration was F/1.5. The ratios of shear moduli were 4.0 and 1.78 in the materials of the panel (a) and (b), respectively. The ratio of Young's moduli was 1.56 in both materials FIG. 12A shows PD as a function of PSF-material orientation for the F/1.5 2D ARFI PSF focal configuration in eight TI materials. For the material with $\mu_L/\mu_T$ and $E_L/E_T$ closest to 1, PD did not depend on the material orientation (dotted square line in FIG. 12A). On the contrary, variability in PD with PSF-AoS orientation was greatest for the material with the highest degree of anisotropy (solid '*' line in FIG. 12A).

FIG. 12B shows PD as a function of material-PSF orientation for angles up to 360° for the F/1.5 2D ARFI PSF focal configuration in three TI materials with fitted sinusoidal function (Peak Displacement=$B_0+B_1 \sin(B_2*Orientation+B_3)$) and root mean square error (RMSE) of the fit. $E_L$, $E_T$, and $\mu_T$ were fixed to 47.16 kPa, 30.231 kPa, and 9 kPa, respectively, whereas $\mu_L$ was varied to 16 (triangle), 36 (circle), and 90 (square) kPa in these three materials. The parameters of the fitted sinusoids were $B_0$=14.34 (triangle), 11.81 (circle), and 8.0 (square); $B_1$=1.37 (triangle), 2.40 (circle), and 2.58 (square); $B_2$=-2.0 (triangle), 2.02 (circle), and 2.04 (square); $B_3$=4.74 (triangle), -1.65 (circle), and -1.69 (square). FIG. 12B similarly shows PD as a function of PSF-AoS orientation for angles up to 360° in three representative materials with increasing degrees of anisotropy. The parameters of sinusoidal functions fit to each material are listed in the caption. RMSE in the sinusoidal fit (see legend) shows that RMSE increases with increasing degree of shear modulus anisotropy. For the least anisotropic material ($\mu_L/\mu_T$=1.78 and $E_L/E_T$=1.56), PD follows an approximately sinusoidal variation pattern as the PSF-AoS orientation angle increases. However, as the material increases in the degree of shear anisotropy, PD variation deviates from a sinusoidal profile when the long axis of the 2D ARFI PSF is aligned along the AoS (90° and 270° orientations). This deviation arises from large changes in PD associated with small changes in orientation angle when the asymmetric 2D ARFI PSF is primarily pushing along the AoS.

Rather than interrogating seven or more different material-PSF orientations, a more practical imaging scenario would entail measuring PD in only two orientations, i.e. with the long axis of the ARFI 2D PSF aligned across (0°) and along (90°) the material's AoS. Then, the ratio of these two PDs can be related to the degree of material anisotropy.

Figures 13A, 13B:
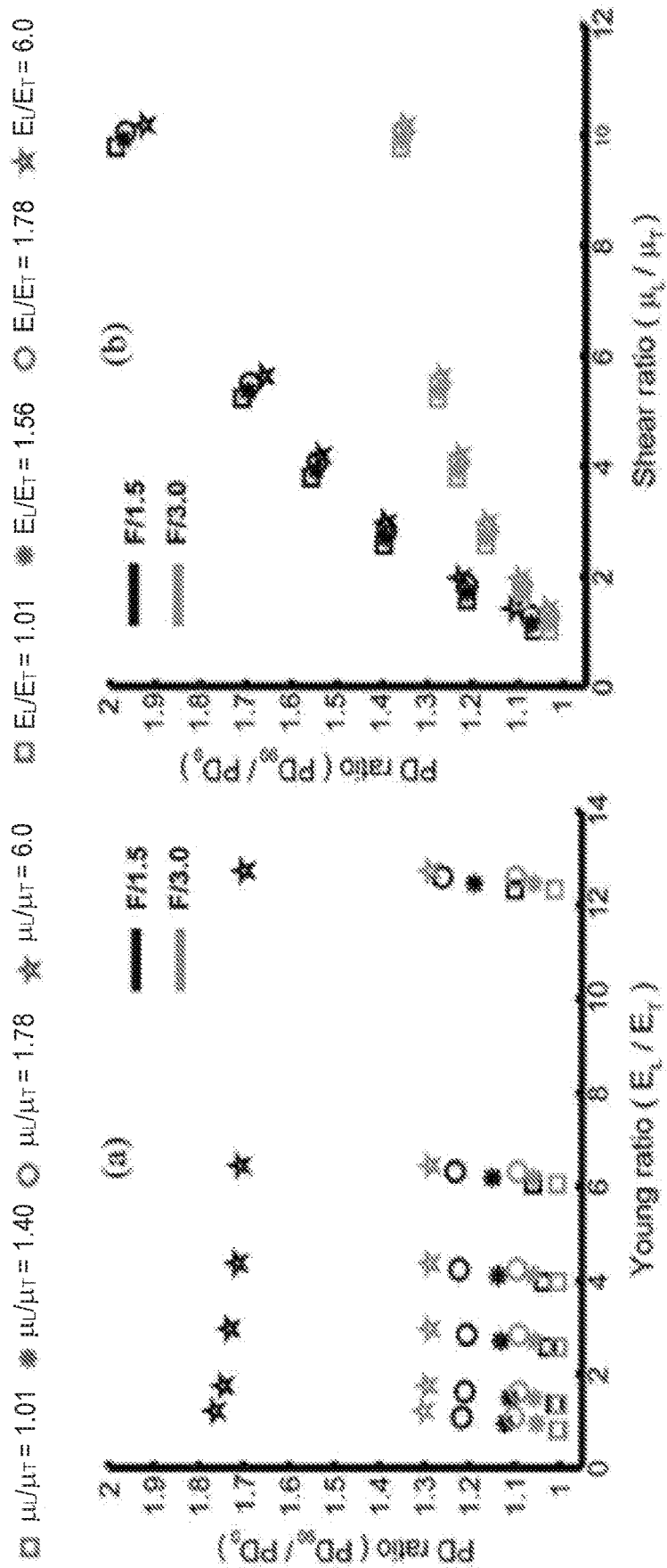
Figures 13C, 13D:
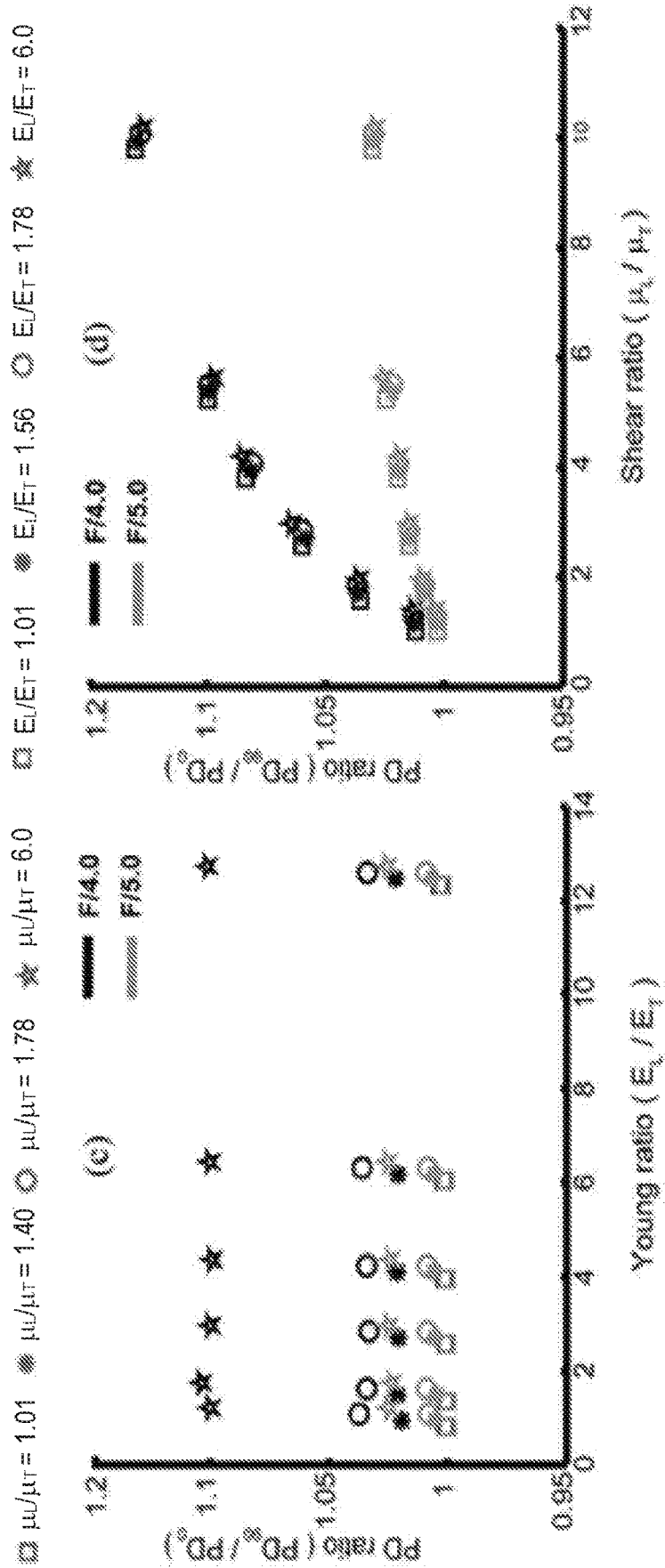

FIGS. 13A through 13D show ratios of PDs ($PD_{90}/PD_0$) versus degree of material anisotropy (ratio of Young's moduli or ratio of shear moduli) for F/1.5 and F/3 (FIGS. 13A and 12B) and for F/4 and F/5 (FIGS. 13C and 13D) 2D ARFI PSF focal configurations. FIGS. 13A and 13C show the impact of anisotropy in Young's modulus on the ratio of PDs when degree of anisotropy in shear modulus is fixed ($\mu_L/\mu_T$=1.01, 1.40, 1.78, and 6.0). FIGS. 13B and 13D show the impact of anisotropy in shear modulus on the ratio of PDs when degree of anisotropy in Young's modulus is fixed ($E_L/E_T$=1.01, 1.56, 1.78, and 6.0). Note that FIGS. 13A and 13B use a different Y-axis scale from that used in FIGS. 13C and 13D.

First, note that for all four 2D ARFI PSF focal configurations, variation in the degree of Young's modulus anisotropy has little impact on $PD_{90}/PD_0$. However, $PD_{90}/PD_0$ increases with increasing degree of anisotropy in shear modulus. Second, for all examined materials, $PD_{90}/PD_0$ is larger when more asymmetric 2D ARFI PSF focal configurations are used.

FIG. 14A shows FEM-derived (dashed lines) and ultrasonically-tracked (solid lines) PD in two representative TI materials as a function of PSF-material orientation for the F/1.5 2D ARFI PSF focal configuration. $E_L$, $E_T$, and $\mu_T$ were fixed to 27.36 kPa, 27.09 kPa, and 9 kPa, respectively, whereas $\mu_L$ was 49 kPa (triangle, gray) or 16 kPa (diamond, black). Ultrasonically-tracked PDs are shown as mean±standard deviation over 10 independent speckle realizations.

FIG. 14B shows FEM-derived (dashed lines) and ultrasonically-tracked (solid lines) ratio of PDs ($PD_{90}/PD_0$) versus the ratio of shear moduli ($\mu_L/\mu_T$) for F/1.5 2D ARFI PSF focal configuration. Ultrasonically-tracked (gray, solid line, triangle) ratio of PDs is shown as mean±standard deviation over 10 independent speckle realizations. $E_L$, $E_T$, and $\mu_T$ were fixed to 27.36 kPa, 27.09 kPa, and 9 kPa, respectively, whereas $\mu_L$ was varied to values of 11, 16, 25, 36, 49, and 90 kPa.

Two observations are notable. First, for both FEM-derived and ultrasonically-tracked cases, PDs follow a similar trend of spanning minimum to maximum values when the AoS is oriented from 0° to 90°. Second, in both materials, ultrasonically-tracked PDs are underestimated, consistent with expectation. However, this displacement underestimation does not substantially influence the ratio of PDs ($PD_{90}/PD_0$), as shown in FIG. 14B, for six simulated TI materials with different ratios of shear moduli ($\mu_L/\mu_T$). The FEM-derived and ultrasonically-tracked ratio of PDs increase similarly with increasing degree of anisotropy in shear modulus.

FIG. 15A shows FEM-derived (dashed lines) and ultrasonically-tracked (solid lines) PD in a representative TI material ($E_L$=27.36 kPa, $E_T$=27.09 kPa, $\mu_L$=36 kPa, and $\mu_T$=9 kPa) as a function of PSF-material orientation for the F/1.5 2D ARFI PSF focal configuration with ARF durations of 25 µs (diamond, black) or 100 µs (triangle, gray). Ultrasonically-tracked PDs are shown as mean±standard deviation over 10 different speckle realizations.

FIG. 15B shows FEM-derived (dashed lines) and ultrasonically-tracked (solid lines) ratio of PDs ($PD_{90}/PD_0$) in the representative material versus ARF duration for F/1.5 2D ARFI PSF focal configuration. FEM-derived ratio of PDs is shown for two PRFs, 40 KHz (time sampling interval=25 µs, diamond) and 10 KHz (time sampling interval=100 µs, square). Ultrasonically-tracked (gray, solid line, triangle) ratio of PDs is shown as mean±standard deviation over 10 different speckle realizations. Tracked (gray, solid line, triangle) ratio of PDs is shown as mean±standard deviation over 10 different speckle realizations.

As expected, the longer ARF duration induces larger PDs. But closer examination reveals that, for both FEM-derived and ultrasonically-tracked cases, the ratio of PDs ($PD_{90}/PD_0$) is larger for the longer duration force. As shown in FIG. 15B, $PD_{90}/PD_0$ is lower for the 25 µs and 50 µs ARF durations than for the 75 µs and 100 µs ARF durations when the PRF is 10 KHz. However, when the PRF is 40 KHz, $PD_{90}/PD_0$ does not vary appreciably with ARF duration.

Discussion

A novel method that exploits ARFI-induced PD to interrogate the degree of anisotropy in TI materials has been developed and evaluated in silico in this manuscript. In this approach, the degree of anisotropy is assessed as the ratio of PD achieved when the long axis of an asymmetric ARFI 2D PSF is aligned along versus across the material's AoS. This new method differs from previous techniques for assessing material anisotropy in that the new approach does not observe shear wave propagation. Therefore, local inhomogeneity and shear wave reflections may not be as confounding to estimates of the degree of anisotropy.

A key finding of this work is that, for asymmetric ARFI 2D PSFs (F/1.5 and F/3.0), the induced PDs and PSs are maximized when the long axis of the PSF is oriented along (90°) and minimized when the long axis is oriented across (0°) the material's AoS, as demonstrated in FIG. 10C. However, for the symmetrical ARFI-2D PSF (F/5.0), induced PD and PS are independent of PSF-AoS orientation because the interaction of the ARFI 2D PSF with the material is consistent (FIG. 10C). This result is meaningful because it suggests that material anisotropy may be selectively interrogated or obviated by implementing asymmetric or symmetric ARFI 2D PSFs, respectively. Interrogating degree of anisotropy is clinically relevant. For example, muscle fiber fragmentation and disordered fatty/fibrous deposition with dystrophic degeneration degrade the SWV derived degree of anisotropy in affected muscles. However, if the material-PSF orientation is not precisely controlled, anisotropy may be confounding in the context of longitudinal and/or cross-sectional study designs. In such scenarios, differences in measurement orientation would confuse true difference in tissue structure or composition. Thus, a symmetric ARFI 2D PSF would be useful to ensure consistent measurement of material property.

Another critical outcome of this work is the demonstration that, for an asymmetrical ARFI 2D PSF, the degree of difference in PDs achieved at 90° and 0° PSF-AoS orientations increases as the degree of anisotropy of the material increases, with consistent PD at 180° increments, as shown in FIGS. 12A and 12B. This result is significant because it suggests that evaluating the difference in achieved PDs, as in the ratio of the PDs for example, reflects true degrees of difference in the directionally-dependent material properties.

It is important to consider that the ratio of PDs is more strongly influenced by anisotropy in shear moduli rather than Young's moduli, as shown in FIGS. 13A through 13D. For focal configurations of F/1.5 and F/3, percent change in the ratio of PD with respect to the percent change in ratio of Young's moduli $$\left( \frac{\Delta \frac{PD_{90}}{PD_0}}{\Delta \frac{E_L}{E_T}} \right)$$

was 0.83% and 0.08%, respectively, when the ratio of shear moduli was fixed to 1.01. However, for the same focal configurations, percent change in the ratio of PDs with respect to the percent change in ratio of shear moduli $$\left( \frac{\Delta \frac{PD_{90}}{PD_0}}{\Delta \frac{\mu_L}{\mu_T}} \right)$$

was 10.5% and 3.72%, respectively, when the ratio of Young's moduli was fixed to 1.01. For F/4 and F/5 focal configurations, the ratio of PDs did not depend on the ratio of Young's moduli (FIG. 13C), but they did increase slightly with increasing ratio of shear moduli when the ratio of Young's moduli was fixed. Percentage change in the ratio of PDs with respect to the change in the ratio of shear moduli $$\left( \frac{\Delta \frac{PD_{90}}{PD_0}}{\Delta \frac{\mu_L}{\mu_T}} \right)$$

was 1.35% and 0.31% for F/4 and F/5 focal configurations, respectively when ratio of Young's moduli was fixed to 1.01. These results suggest that our approach is more sensitive to degree of anisotropy in shear modulus than Young's modulus.

Although the data presented herein show that $PD_{90}/PD_0$ reflects the ratio of shear and, to a lesser extent, Young's moduli, a quantitative relationship between these terms has not been developed. Rather, the described approach is relevant to distinguishing materials in terms of their relative degrees of anisotropy.

The analyses presented up to FIGS. 13A and 13B were applied directly to the FEM simulated material deformations, without accounting for ultrasonic displacement tracking. It is well established that ultrasonically tracked tissue deformation is subject to jitter and displacement underestimation errors. Indeed, the ultrasonically-tracked displacements have variance (jitter) and are underestimated. However, despite these errors, the ultrasonically-tracked PDs increase with increasing material orientation angle in a manner similar to the FEM-derived PDs. Moreover, the ratios of PDs ($PD_{90}/PD_0$) in six different TI materials do not substantially differ between FEM-derived and ultrasonically-tracked measures. These data suggest that, even when ultrasonically-tracked, ARFI-induced PDs reflect the degree of anisotropy in TI materials.

One area requiring further investigation is the potential impact of orientation-dependent differences in displacement magnitude that could disproportionately influence the magnitude of jitter error in $PD_{90}$ versus $PD_0$ measures. Jitter magnitude is inversely related to the correlation coefficient, which decreases with increasing displacement. Therefore, jitter could be larger when the long-axis of the asymmetrical ARFI 2D PSF is aligned along versus across the AoS, which could corrupt PD ratios. Jitter magnitude is also inversely related to center frequency, fractional bandwidth, SNR, and kernel length. Implementing methods to control for jitter error may be necessary when extending this work to experimental realization. For example, averaging displacement profiles across space and time, maximizing SNR, and minimizing displacement magnitude will serve to drive down jitter to support experimental assessment of the degree of anisotropy.

Another topic for deeper study is the possible impact of orientation-dependent differences in shear wave speed that could disproportionately influence the degree of displacement underestimation in $PD_{90}$ versus $PD_0$ measures. Displacement underestimation will be less severe when the long axis of the ARFI 2D PSF is oriented along versus across the material's AoS due to faster shear wave propagation and, therefore, resolution of shearing artifacts under the tracking PSF. Such displacement underestimation could be minimized by tracking with tighter focal configurations than the ARFI excitation, which would be achievable using matrix array transducers capable of elevational focusing.

In addition to ultrasonically tracking ARFI-induced displacements, another confounding factor is misalignment. During in vivo imaging, it may be difficult to align the long axis of the asymmetrical ARFI 2D PSF along and across the AoS, and misalignment will introduce error in the assessment of anisotropy degree. In FIG. 12A, for the most anisotropic material (solid line 'o'), a 15° error in alignment (75° instead of 90°) introduces roughly 10% error in the perceived peak displacement at 90° and an associated 9% error in $PD_{90}/PD_0$. A potential solution is to rotate the imaging transducer through multiple orientation angles to identify the orientations that achieve the largest) (90°) and smallest (0°) displacements.

FIGS. 15A and 15B point out another relevant consideration when relating ARFI-induced PDs to the degree of anisotropy in TI materials. While the duration of the ARF excitation does not directly impact the ratios of PDs ($PD_{90}/PD_0$) achieved in linearly elastic materials, measurements of $PD_{90}/PD_0$ are effected by the temporal relationship of the ARF duration to the PRF. To understand this, consider that for the shorter (25 µs and 50 µs) ARF durations with a 10 KHz PRF, more time elapses for elastic recovery between ARF cessation and temporal sampling of induced-displacement than for the longer (75 µs and 100 µs) ARF durations. Thus, peak displacement is more severely underestimated when using the shorter versus the longer ARF durations due to greater temporal sampling error. When the simulated PRF is increased to 40 KHz, temporal sampling error is reduced, and $PD_{90}/PD_0$ measures are more consistent over ARF durations. These results show the importance of the temporal sampling period, and its optimization is a topic of ongoing investigation. Finally, the simulated materials that were evaluated in this study were purely elastic. The impact of viscosity on the estimation of anisotropy as a ratio of ARFI-derived PDs is yet to be determined.

In this in silico study, a novel method for assessing the degree of anisotropy in elastic TI materials using ARFI-induced PDs is presented. The results demonstrate that for asymmetrical ARFI 2D PSFs, that the ratio of PDs (and PSs) achieved with the long axis of the PSF aligned along versus across the material's AoS ($PD_{90}/PD_0$) qualitatively reflects the degree of anisotropy in the shear and, to a lesser extent, Young's moduli of the material. This may be useful for diagnostic purposes, particularly in tissues and organs such as muscle in which degree of anisotropy degrades with disease progression. Further, this work shows that it is possible to selectively obviate material anisotropy by using symmetrical ARFI excitations. Thus, symmetrical ARFI focal configurations may be desirable when the orientation of the ARFI excitation to the material's AoS is not specifically known and standardization of measurement is important, such as for longitudinal or cross-sectional studies of anisotropic tissues and organs. The feasibility of extension to experimental realization is demonstrated by simulating ultrasonic tracking of ARFI-induced displacements and by varying the ARF duration. Overall, this study demonstrates that ARFI-derived PD is relevant to interrogating anisotropy in elastic TI materials.

TABLE 2

| Material Number | $E_L/E_T$ | $\mu_L/\mu_T$ | $E_L$ | $E_T$ | $\mu_L$ | $\mu_T$ | $v_{TT}$ |
|---|---|---|---|---|---|---|---|
| 1 | 1.01 | 1.22 | 27.36 | 27.09 | 11.0 | 9.0 | 0.505 |
| 2 | 1.01 | 1.78 | 27.36 | 27.09 | 16.0 | 9.0 | 0.505 |
| 3 | 1.01 | 2.78 | 27.36 | 27.09 | 25.0 | 9.0 | 0.505 |
| 4 | 1.01 | 4.0 | 27.36 | 27.09 | 36.0 | 9.0 | 0.505 |
| 5 | 1.01 | 5.44 | 27.36 | 27.09 | 49.0 | 9.0 | 0.505 |
| 6 | 1.01 | 10.0 | 27.36 | 27.09 | 90.0 | 9.0 | 0.505 |
| 7 | 1.56 | 1.22 | 47.16 | 30.23 | 11.0 | 9.0 | 0.679 |
| 8 | 1.56 | 1.78 | 47.16 | 30.23 | 16.0 | 9.0 | 0.679 |
| 9 | 1.56 | 2.78 | 47.16 | 30.23 | 25.0 | 9.0 | 0.679 |
| 10 | 1.56 | 4.0 | 47.16 | 30.23 | 36.0 | 9.0 | 0.679 |
| 11 | 1.56 | 5.44 | 47.16 | 30.23 | 49.0 | 9.0 | 0.679 |
| 12 | 1.56 | 10.0 | 47.16 | 30.23 | 90.0 | 9.0 | 0.679 |
| 13 | 1.78 | 1.22 | 55.08 | 30.94 | 11.0 | 9.0 | 0.719 |
| 14 | 1.78 | 1.78 | 55.08 | 30.94 | 16.0 | 9.0 | 0.719 |
| 15 | 1.78 | 2.78 | 55.08 | 30.94 | 25.0 | 9.0 | 0.719 |
| 16 | 1.78 | 4.0 | 55.08 | 30.94 | 36.0 | 9.0 | 0.719 |
| 17 | 1.78 | 5.44 | 55.08 | 30.94 | 49.0 | 9.0 | 0.719 |
| 18 | 1.78 | 10.0 | 55.08 | 30.94 | 90.0 | 9.0 | 0.719 |
| 19 | 6.0 | 1.22 | 207.0 | 34.50 | 11.0 | 9.0 | 0.917 |
| 20 | 6.0 | 1.78 | 207.0 | 34.50 | 16.0 | 9.0 | 0.917 |
| 21 | 6.0 | 2.78 | 207.0 | 34.50 | 25.0 | 9.0 | 0.917 |
| 22 | 6.0 | 4.0 | 207.0 | 34.50 | 36.0 | 9.0 | 0.917 |
| 23 | 6.0 | 5.44 | 207.0 | 34.50 | 49.0 | 9.0 | 0.917 |
| 24 | 6.0 | 10.0 | 207.0 | 34.50 | 90.0 | 9.0 | 0.917 |
| 25 | 12.53 | 1.78 | 275.95 | 22.02 | 10.0 | 5.62 | 0.960 |
| 26 | 6.25 | 1.78 | 188.76 | 30.20 | 14.0 | 7.87 | 0.920 |
| 27 | 4.17 | 1.78 | 158.56 | 38.02 | 18.0 | 10.11 | 0.880 |
| 28 | 2.78 | 1.78 | 125.08 | 44.99 | 22.0 | 12.36 | 0.820 |
| 29 | 1.56 | 1.78 | 76.54 | 49.06 | 26.0 | 14.61 | 0.679 |
| 30 | 1.02 | 1.78 | 51.91 | 50.89 | 30.0 | 16.85 | 0.510 |
| 31 | 12.53 | 1.40 | 350.86 | 28.01 | 10.0 | 7.14 | 0.960 |
| 32 | 6.25 | 1.40 | 240.00 | 38.40 | 14.0 | 10.0 | 0.920 |
| 33 | 4.17 | 1.40 | 201.60 | 48.35 | 18.0 | 12.86 | 0.880 |
| 34 | 2.78 | 1.40 | 159.03 | 57.21 | 22.0 | 15.71 | 0.820 |
| 35 | 1.56 | 1.40 | 97.31 | 62.38 | 26.0 | 18.57 | 0.679 |
| 36 | 1.02 | 1.40 | 66.00 | 64.71 | 30.0 | 21.43 | 0.510 |
| 37 | 12.53 | 1.01 | 486.34 | 38.81 | 10.0 | 9.90 | 0.960 |
| 38 | 6.25 | 1.01 | 332.67 | 53.23 | 14.0 | 13.86 | 0.920 |
| 39 | 4.17 | 1.01 | 279.45 | 67.01 | 18.0 | 17.82 | 0.880 |
| 40 | 2.78 | 1.01 | 220.44 | 79.29 | 22.0 | 21.78 | 0.820 |
| 41 | 1.56 | 1.01 | 134.89 | 86.47 | 26.0 | 25.74 | 0.679 |
| 42 | 1.02 | 1.01 | 91.49 | 89.69 | 30.0 | 29.70 | 0.510 |
| 43 | 12.53 | 6.0 | 81.87 | 6.53 | 10.0 | 1.67 | 0.960 |
| 44 | 6.25 | 6.0 | 56.00 | 8.96 | 14.0 | 2.33 | 0.920 |
| 45 | 4.17 | 6.0 | 47.04 | 11.28 | 18.0 | 3.0 | 0.880 |
| 46 | 2.78 | 6.0 | 37.11 | 13.35 | 22.0 | 3.67 | 0.820 |
| 47 | 1.56 | 6.0 | 22.71 | 14.56 | 26.0 | 4.33 | 0.679 |

TABLE 2-continued

| Material Number | $E_L/E_T$ | $\mu_L/\mu_T$ | $E_L$ | $E_T$ | $\mu_L$ | $\mu_T$ | $v_{TT}$ |
|---|---|---|---|---|---|---|---|
| 48 | 1.02 | 6.0 | 15.40 | 15.10 | 30.0 | 5.0 | 0.510 |
| 49 | 8.33 | 5.70 | 91.0 | 10.92 | 16.0 | 2.81 | 0.94 |
| 50 | 1.67 | 1.01 | 91.0 | 54.0 | 16.0 | 15.85 | 0.703 |
| 51 | 5.88 | 3.99 | 91.0 | 15.35 | 16.0 | 4.01 | 0.92 |
| 52 | 2.63 | 2.13 | 72.29 | 27.18 | 16.0 | 7.50 | 0.813 |

Partial Angle Measurements

Although the examples described above generally involve comparing measurements taken at 0° and 90° relative to each other, the techniques described herein also work with measurements that are not a right angles to each other, and also work with measurements that are taken at angles other than 0° and 90° relative to the direction of anisotropy to the material being measured.

In one experiment, PD as a function of material-PSF orientation was measured in two representative TI materials with ratio of shear moduli (SR=$\mu_L/\mu_T$) 1.72 and 5.9. The degree of anisotropy was successfully derived using PD and SWV in three simulated material using rotation angle=90°, 30°, 15°. The ratios of SWV at 0° to SWVs at 15°, 30°, and 90° were used to calculate SWV derived degree of anisotropy because PD and SWV are inversely related. Degree of anisotropy of material with SR=1.22 was compared against degree of anisotropy of materials with SR=1.78 and 2.78. PD was measured as a function of material orientation in the swine psoas major muscle, and the degree of anisotropy was derived using the measured PD and SWV in an isotropic elastic phantom and muscle.

Increasing Axial Measurement Range

FIG. 16 is a graph of the degree of asymmetry of an ARF excitation as a function of depth, where the focal depth is 35 mm. As FIG. 16 illustrates, the degree of asymmetry of the ARF excitation is relatively constant through depth. For example, in FIG. 16, the degree of asymmetry remains at approximately 0.25 from a depth of 5 mm to a depth of 33 mm. This allows for anisotropy imaging in a large region above the focal depth.

Rotation-Less Measurements

In one embodiment, the variation in degree of asymmetry of an ARF excitation as a function of depth is exploited so as to perform measurements at different relative orientations without the need to physically rotate the ultrasonic transducer. Because the transducer's position is not changed between the two measurements, the two measurements are always properly registered to each other.

FIG. 17 is a graph of the degree of asymmetry of an ARF excitation as a function of depth for five different excitations, each having a different focal depth. At an observation depth of 33 mm, setting a focal depth of 33 mm creates an ARF having a "tall oval" shape at the observation depth of 33 mm; setting a focal depth to 38 mm creates an ARF having a "wide oval" shape at the observation depth of 33 mm. Thus, by changing the focal depth only, forces having long axes 90° apart can be created without having to rotate the transducer. This technique can provide very accurate results by eliminating errors due to unintended translation of the transducer during rotation, for example.

Experimental and Clinical Results

The techniques above have been shown to detect skeletal and muscle anisotropy in the presence of Duchenne Muscular Dystrophy (DMD). It has been demonstrated that the ratio of Relative Elasticity (RE) at the focal depth in both Rectus Femorus and Gastrocnemius Medial Head (GM) muscles. The DMD Rectus Femorus was significantly more anisotropic than the control muscles. Also, the transverse shear modulus was higher than the longitudinal shear modulus in the DMD Rectus Femorus, yielding a ratio greater than 1.0, which is the opposite to that of healthy muscle. In the GM, the anisotropy ratio was not significantly different between DMD and control muscles.

In another study, the ratios of PDs (PDalong/PDacross) achieved using an asymmetrical F/1.5 ARF focal configuration were linearly correlated (R2=1) to the ratios of SWVs (SWValong/SWVacross) in surgically exposed pig kidneys, in vivo. PD ratios measured in vivo in 3 pig kidneys and in 11 renal transplant patients using an asymmetrical F/1.5 ARF focal configuration is greater than 1, while the ratios achieved using a symmetrical F/5.0 ARF focal configuration are approximately 1. In patients, the F/1.5 and F/5.0 PD ratios were statistically different. PD ratios measured in vivo in 8 renal transplant patients using an asymmetrical F/1.5 ARF focal configuration at 1 month and three months after transplantation did not statistically differ. The transplants had stable creatinine levels and renal function at one and three months post-transplant; the transplants were excluded if rejection was detected clinically.

Those skilled in the art will recognize improvements and modifications to the preferred embodiments of the present invention. All such improvements and modifications are considered within the scope of the concepts disclosed herein and the claims that follow.

What is claimed is:

1. A method for assessing a material anisotropy, the method comprising:
    applying a first force to a material sample and taking a first displacement measurement, the first force having a direction, having a coronal plane normal to the direction of the first force, and having an oval or other profile with long and short axes within the coronal plane, the long axis being oriented in a first direction within the coronal plane;
    applying a second force to the material sample and taking a second displacement measurement, the second force having a direction, having a coronal plane normal to the direction of the second force, and having an oval or other profile with long and short axes within the coronal plane, the long axis being oriented in a second direction within the coronal plane different from the first direction of the first force; and
    calculating the material anisotropy based on the first and second displacement measurements, wherein the first force and the second force are applied in any order,
    wherein the first and second displacement measurements comprise:
    measurements of displacement;
    measurements of relaxation time constant for constant stress (Tau);
    measurements of recovery time;
    measurements of strain;
    measurements of elasticity; or
    measurements of viscosity.

2. The method of claim 1 wherein the material sample comprises a tissue sample.

3. The method of claim 1 wherein calculating the material anisotropy based on the first and second displacement measurements comprises calculating the material anisotropy based on a ratio of the larger of two measurements to the smaller of two measurements.

4. The method of claim 1 wherein calculating the material anisotropy comprises calculating an elasticity anisotropy and/or a viscosity anisotropy.

5. The method of claim 1 wherein the coronal plane is at a focal depth within the material sample.

6. The method of claim 1 wherein a direction of anisotropy of the material sample is known and wherein the first force has an orientation at a known angle relative to the direction of anisotropy of the material.

7. The method of claim 1 wherein a direction of anisotropy of the material sample is unknown and wherein the method further comprises sweeping an angle of orientation of a long axis of force within the coronal plane until two different measurements are taken at a known difference in angle of orientation, and using the two different measurements and known difference in angle of orientation to calculate the material anisotropy.

8. The method of claim 1 wherein a direction of anisotropy of the material sample is unknown and wherein the method further comprises sweeping an angle of orientation of a long axis of force within the coronal plane until maximum and minimum measurements are taken, and using the maximum and minimum measurements to calculate the material anisotropy.

9. The method of claim 1 wherein at least one of the first or second forces is applied using at least one of:
a mechanical indenter;
a magnetic field;
an acoustic radiation force; and
an ultrasound transducer.

10. The method of claim 1 wherein the at least one of the first and second forces are applied using an ultrasound transducer.

11. The method of claim 10 wherein the first force is applied at a first focal depth, wherein the second force is applied at a second focal depth, and wherein the first focal depth is the same as the second focal depth or different from the second focal depth.

12. The method of claim 10 wherein a position and an orientation of the ultrasound transducer are the same during application of the first force and the second force.

13. The method of claim 10 wherein the ultrasound transducer comprises a plurality of emitter elements arranged in a one-dimensional or two-dimensional configuration.

14. The method of claim 13 wherein a direction of the long axis of the first force is controlled by rotation of the ultrasound transducer about an axis normal to the coronal plane.

15. The method of claim 13 wherein a direction of the long axis of the first force is controlled without rotation of the ultrasound transducer about an axis normal to the coronal plane.

16. The method of claim 1 wherein at least one of the first or second displacement measurements is taken using at least one of:
ultrasound;
magnetic resonance imaging (MRI);
an optical method;
optical coherence tomography (OCT);
a mechanical micrometer; and
an optical microscope.

17. The method of claim 1 wherein the step of applying the first force and taking the first displacement measurement is performed a plurality of times to produce a plurality of first displacement measurements, wherein the step of applying the second force and taking the second displacement measurement is applied a plurality of times, and wherein a material viscosity anisotropy is calculated based on the plurality of first and second displacement measurements.

18. A system for assessing a material anisotropy, the system being adapted to comprising:
one or more processors; and
memory storing instructions executable by the one or more processors, whereby the system is operable to:
apply a first force to a material sample and take a first displacement measurement, the first force having a direction, having a coronal plane normal to the direction of the first force, and having an oval or other profile with long and short axes within the coronal plane, the long axis being oriented in a first direction within the coronal plane;
apply a second force to the material sample and take a second displacement measurement, the second force having a direction, having a coronal plane normal to the direction of the second force, and having an oval or other profile with long and short axes within the coronal plane, the long axis being oriented in a second direction within the coronal plane different from the first direction of the first force; and
calculate the material anisotropy based on the first and second displacement measurements, wherein the first force and the second force are applied in any order,
wherein the first and second displacement measurements comprise:
measurements of displacement;
measurements of relaxation time constant for constant stress (Tau);
measurements of recovery time;
measurements of strain;
measurements of elasticity; or
measurements of viscosity.

19. A non-transitory computer readable medium storing software instructions that, when executed by one or more processors of a system for assessing material anisotropy, cause the system to:
apply a first force to a material sample and take a first displacement measurement, the first force having a direction, having a coronal plane normal to the direction of the first force, and having an oval or other profile with long and short axes within the coronal plane, the long axis being oriented in a first direction within the coronal plane;
apply a second force to the material sample and take a second displacement measurement, the second force having a direction, having a coronal plane normal to the direction of the second force, and having an oval or other profile with long and short axes within the coronal plane, the long axis being oriented in a second direction within the coronal plane different from the first direction of the first force; and
calculate a material anisotropy based on the first and second displacement measurements, wherein the first force and the second force are applied in any order,
wherein the first and second displacement measurements comprise:

measurements of displacement;
measurements of relaxation time constant for constant stress (Tau);
measurements of recovery time;
measurements of strain;
measurements of elasticity; or
measurements of viscosity.

\* \* \* \* \*